US008937087B2

(12) United States Patent
Shiraki et al.

(10) Patent No.: US 8,937,087 B2
(45) Date of Patent: Jan. 20, 2015

(54) HETEROCYCLIC ACETAMIDE COMPOUND

(71) Applicant: Astellas Pharma Inc., Tokyo (JP)

(72) Inventors: Ryota Shiraki, Tokyo (JP); Takahiko Tobe, Tokyo (JP); Shimpei Kawakami, Tokyo (JP); Hiroyuki Moritomo, Tokyo (JP); Makoto Ohmiya, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/256,135

(22) Filed: Apr. 18, 2014

(65) Prior Publication Data

US 2014/0315963 A1 Oct. 23, 2014

(30) Foreign Application Priority Data

Apr. 18, 2013 (JP) .................. 2013-087151

(51) Int. Cl.
  *C07D 413/12* (2006.01)
  *C07D 417/12* (2006.01)

(52) U.S. Cl.
  CPC ............ *C07D 417/12* (2013.01); *C07D 413/12* (2013.01)
  USPC .......................................... 514/325; 548/126

(58) Field of Classification Search
  None
  See application file for complete search history.

(56) References Cited

U.S. PATENT DOCUMENTS

| | | | |
|---|---|---|---|
| 6,380,210 | B1 | 4/2002 | DeSimone et al. |
| 6,627,624 | B1 | 9/2003 | DeSimone et al. |
| 2003/0092912 | A1 | 5/2003 | DeSimone et al. |
| 2004/0023993 | A1 | 2/2004 | DeSimone et al. |
| 2004/0058820 | A1 | 3/2004 | Hagmann et al. |
| 2005/0234061 | A1 | 10/2005 | Hagmann et al. |
| 2006/0160842 | A1 | 7/2006 | DeSimone et al. |
| 2007/0299118 | A1 | 12/2007 | Starck et al. |
| 2008/0171692 | A1 | 7/2008 | Hagmann et al. |
| 2008/0269280 | A1 | 10/2008 | Zhang et al. |
| 2009/0163535 | A1 | 6/2009 | Van Zandt et al. |
| 2009/0258884 | A1 | 10/2009 | Hagmann et al. |
| 2009/0275571 | A1 | 11/2009 | Goodman et al. |
| 2010/0256130 | A1 | 10/2010 | Goodman et al. |
| 2010/0280030 | A1 | 11/2010 | Schadt et al. |
| 2011/0263596 | A1 | 10/2011 | Schadt et al. |

FOREIGN PATENT DOCUMENTS

| | | |
|---|---|---|
| JP | 2001/139574 | 5/2001 |
| JP | 2002-541151 A | 12/2002 |
| JP | 2005-519958 A | 7/2005 |
| JP | 2008-500300 A | 1/2008 |
| JP | 2009-544623 A | 12/2009 |
| JP | 2010-529051 A | 8/2010 |
| WO | WO00/59905 | 10/2000 |
| WO | WO03/024929 A1 | 3/2003 |
| WO | WO03/077847 A2 | 9/2003 |
| WO | WO03/077847 A3 | 9/2003 |
| WO | WO2004/082605 A2 | 9/2004 |
| WO | WO2004/082605 A3 | 9/2004 |
| WO | WO2005/080334 A1 | 9/2005 |
| WO | WO2005/118561 A1 | 12/2005 |
| WO | WO2007/022257 A2 | 2/2007 |
| WO | WO2007/022257 A3 | 2/2007 |
| WO | WO2007/073432 A2 | 6/2007 |
| WO | WO2007/073432 A3 | 6/2007 |
| WO | WO2008/011551 A1 | 1/2008 |

OTHER PUBLICATIONS

International Search Report issued in PCT/JP2014/061007, 7 pp.
Written Opinion of the ISA with a partial English translation issued in PCT/JP2014/061007, 7 pp.
Takayuki Fukaya, et al., Design, synthesis and structure-activity relationships of novel benzoxazolone derivatives as 18 kDa translocator protein (TSPO) ligands; Bioorganic & Medicinal Chemistry, vol. 20(2012), pp. 5568-5582.

*Primary Examiner* — Noble Jarrell
(74) *Attorney, Agent, or Firm* — Oblon, Spivak, McClelland, Maier & Neustadt, L.L.P.

(57) ABSTRACT

[Problem] A compound which is useful as a dopamine D1 receptor positive allosteric modulator (D1 PAM) is provided. [Means for Solution] The present inventors have studied a compound which has a dopamine D1 receptor positive allosteric modulating activity and is useful as an active ingredient of a pharmaceutical composition for preventing and/or treating cognitive impairment, negative symptoms of schizophrenia, Parkinson's disease, Alzheimer's disease, Huntington's disease, drug addictions, or the like, and they have thus found that a heterocyclic acetamide compound has a dopamine D1 receptor positive allosteric modulating activity, thereby completing the present invention. The heterocyclic acetamide compound of the present invention has a dopamine D1 receptor positive allosteric modulating activity and can be used as an agent for preventing and/or treating cognitive impairment, negative symptoms of schizophrenia, Parkinson's disease, Alzheimer's disease, Huntington's disease, drug addictions, or the like.

12 Claims, No Drawings

HETEROCYCLIC ACETAMIDE COMPOUND

TECHNICAL FIELD

The present invention relates to a heterocyclic acetamide compound which is useful as an active ingredient of a pharmaceutical composition, in particular, a pharmaceutical composition for preventing and/or treating cognitive impairment, negative symptoms of schizophrenia, Parkinson's disease, Alzheimer's disease, Huntington's disease, drug addictions, or the like.

BACKGROUND ART

Dopamine receptors are one kind of G protein-coupled receptors that are present in the central nerve system. The dopamine receptors are classified into the dopamine D1 receptor-like family and the dopamine D2 receptor-like family. Dopamine D1 and D5 receptors in the dopamine receptors belong to the dopamine D1 receptor-like family. Further, dopamine D2, D3 and D4 receptors belong to the dopamine D2 receptor-like family.

It has been reported that the dopamine D1 receptor is coupled with Gαs which is a promoting G protein, thereby activating an adenylate cyclase and increasing the production of intracelluar cAMP to promote the activity of a protein kinase A and exert various functions (Medicinal Research Reviews, 2009, 29(2), p. 272-294).

There is a report suggesting that in patients with schizophrenia, dopamine D1 receptors are significantly decreased in a part of the frontal lobe called the prefrontal cortex and that the degree of decrease in the dopamine D1 receptors is correlated with the intensity of negative symptoms of schizophrenia or the performance of the Wisconsin Card Sorting Test which is a test on functions of the frontal lobe, and as a result, the decrease in dopamine D1 receptors in the prefrontal cortex plays an important role in cognitive impairment or negative symptoms of schizophrenia (Nature, 1997, Feb. 13, 385(6617), p. 634-636).

There are reports suggesting that dopamine D1 receptor agonists are useful in cognitive impairment models (European Neuropsychopharmcology, 2009, 19(6), p. 440-450; Psychopharmacology, 2010, 210(3), p. 407-418; Molecular Pharmacology, 2007, 71(6), p. 1598-1609).

There are also reports suggesting that dopamine D1 receptors are involved in negative symptoms of schizophrenia (The American Journal of Psychiatry, 2002, 159(5), p. 761-767; Pharmacopsychiatry, 2006, 39(3), p. 115-116).

Accordingly, the dopamine D1 receptor agonists are expected as an agent for ameliorating cognitive impairment or negative symptoms of schizophrenia by stimulating the dopamine D1 receptors in the prefrontal cortex.

There are also reports suggesting the possibility of applying dopamine D1 receptor agonists to Parkinson's disease (Current Opinion in Investigational Drugs, 2001, 2(11), p. 1582-1591) or Alzheimer's disease (The Journal of Biological Chemistry, 2011, 286(5), p. 3270-3276).

Furthermore, there are reports that dopamine D1 receptor agonists exhibit effectiveness with the respective animal models with Huntington's disease (Neurodegenerative Diseases, 2011, 8(4), p. 230-239) or drug addictions (Neuroscience Letters, 2012, 513(2), p. 214-218).

Furthermore, there is also a suggestion of the possibility of applying dopamine D1 receptor agonists to cognitive impairment in attention deficit hyperactivity disorder (ADHD) (Neuropsychologia, 2013, 51(2), p. 235-266).

Accordingly, compounds stimulating the dopamine D1 receptors are considered to be promising as a drug for preventing and/or treating diseases such as cognitive impairment, negative symptoms of schizophrenia, Parkinson's disease, Alzheimer's disease, Huntington's disease, drug addictions, or the like.

There are cases where dopamine D1 receptor agonists are also used as a peripheral antihypertensive (The New England Journal of Medicine, 2001, 345(21), p. 1548). On the other hand, for example, there is a report that dihydrexidine which is a dopamine D1 receptor agonist has side effects affecting blood pressure (Clinical Neuropharmacology, 1998, 21(6), p. 339-343).

G Protein-coupled receptors have been studied as an important target for drug discovery for a long period of time. In recent years, it has been found that many G protein-coupled receptors have allosteric sites other than orthosteric ligand sites (ACS Chemical Biology, 2008, 3(9), p. 530-541). Accordingly, drug discovery which targets an allosteric site in a G protein-coupled receptor as a drug discovery target has been actively studied (British Journal of Pharmacology, 2012, 165(6), p. 1659-1669).

A positive allosteric modulator (hereinafter referred to as PAM in some cases) is a compound which binds to a site other than a site to which an endogenous ligand binds with respect to a receptor, thereby enhancing the receptor function. PAM does not increase the receptor function in itself, but increases the receptor function in the presence of a ligand.

Therefore, a dopamine D1 receptor PAM (hereinafter referred to as D1 PAM in some cases) has a dopamine D1 receptor positive allosteric modulating activity, can be used for preventing and/or treating cognitive impairment, negative symptoms of schizophrenia, Parkinson's disease, Alzheimer's disease, Huntington's disease, drug addictions, and the like, and is expected to be useful as a drug having fewer side effects, as compared with dopamine D1 receptor agonists.

In Patent Document 1, it is reported that a compound of the formula (A) has benzodiazepine ω3 receptor agonistic action. In Claims, anti-anxiety or anti-depressant is described. However, there is no specific disclosure of the compound of the present invention.

[Chem. 1]

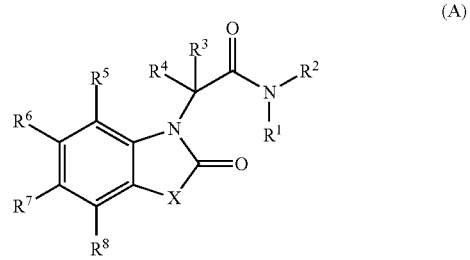

(A)

(in which $R^1$ and $R^2$ each independently represent H, an alkyl group which may be substituted, or the like. X represents O, S, $NR^{10}$, or $CR^{11}R^{12}$. Refer to this publication for the other symbols.)

In Patent Document 2, it is reported that a compound of the formula (B) exhibits a urotensin II agonistic and inhibitory action, and is useful in congestive heart failure or the like.

[Chem. 2]

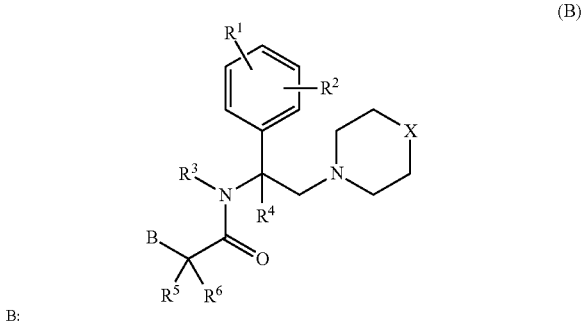

B:

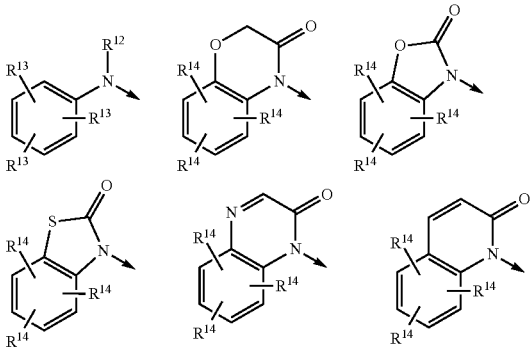

(Refer to this publication for the symbols in the formula.)

In Patent Document 3, it is reported that a compound of the formula (C) exhibits a cannabinoid 1 agonistic and/or inverse agonistic action, and is useful as a central functional agent or the like.

[Chem. 3]

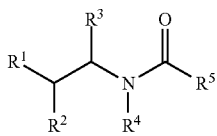

(in which $R^1$ and $R^2$ are each alkyl, cycloalkyl, aryl, arylalkyl, heteroaryl, heteroaryl-alkyl, or the like. Refer to this publication for the other symbols.)

In Patent Document 4, it is reported that a compound of the formula (D) is useful for treating and/or preventing movement disorder and/or movement fluctuations.

[Chem. 4]

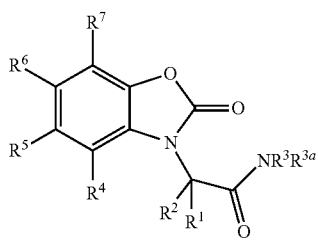

(in which $R^3$ and $R^{3a}$ are each H or unsubstituted $C_{1-4}$ alkyl. Refer to this publication for the other symbols.)

In Patent Document 5, it is reported that a compound of the formula (E) is useful for treating and/or preventing anxiety, depression, cognitive impairment, or the like as a $GABA_A$ modulator.

[Chem. 5]

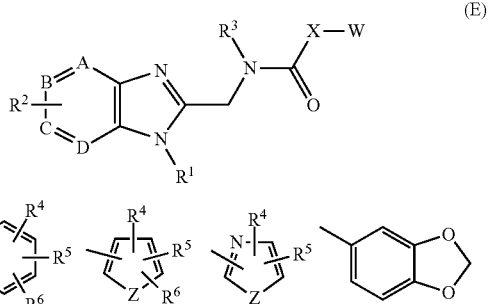

(in which A, B, C, and D represent N or CH. X is a bond, $CH_2$, or CHCH. $R^1$ is Ph, $C_{1-6}$ alkyl, or the like. Refer to this publication for the other symbols.)

RELATED ART

Patent Document

[Patent Document 1] WO 2005/080334
[Patent Document 2] WO 2008/011551
[Patent Document 3] WO 03/077847
[Patent Document 4] WO 2005/118561
[Patent Document 5] WO 00/59905

DISCLOSURE OF INVENTION

Problems to be Solved by the Invention

A compound which is useful as an active ingredient of a pharmaceutical composition, in particular, a pharmaceutical composition for preventing and/or treating cognitive impairment, negative symptoms of schizophrenia, Parkinson's disease, Alzheimer's disease, Huntington's disease, and drug addictions is provided.

Means for Solving the Problems

The present inventors have conducted extensive studies on a compound having a positive allosteric modulating activity on a dopamine D1 receptor, and as a result, they have found that the heterocyclic acetamide compound of the present invention has a positive allosteric modulating activity on a dopamine D1 receptor, thereby completing the present invention.

That is, the present invention relates to a compound of the formula (I) or a salt thereof, and a pharmaceutical composition comprising a compound of formula (I) or a salt thereof and an excipient.

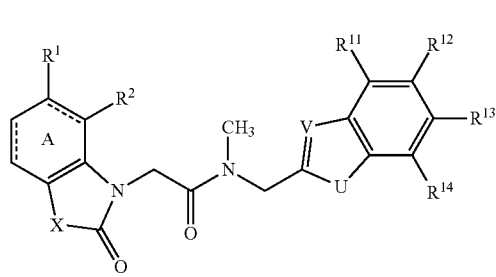

(wherein
ring A is a benzene ring,
$R^1$ is lower alkyl, halogen, halogeno-lower alkyl, or —O-halogeno-lower alkyl,
$R^2$ is H or halogen,
$R^{11}$, $R^{12}$, $R^{13}$ and $R^{14}$ are the same as or different from each other, and are H, lower alkyl, halogen, halogeno-lower alkyl, cycloalkyl, —O-lower alkyl, or —O-halogeno-lower alkyl,
U is $NR^{15}$ or O,
V is CH or N,
in the case where U is P, V is N,
$R^{15}$ is H, lower alkyl, or -lower alkylene-OH, and
X is O).

Further, unless specifically described otherwise, when symbols in one formula in the present specification are also used in other formulae, same symbols denote same meanings.

Moreover, the present invention relates to a pharmaceutical composition for preventing and/or treating cognitive impairment, negative symptoms of schizophrenia, Parkinson's disease, Alzheimer's disease, Huntington's disease, and drug addictions, which comprises a compound of the formula (I) or a salt thereof.

Further, the said pharmaceutical composition includes an agent for preventing and/or treating cognitive impairment, negative symptoms of schizophrenia, Parkinson's disease, Alzheimer's disease, Huntington's disease, and drug addictions, which comprises a compound of the formula (I) or a salt thereof.

Furthermore, the present invention relates to:
(1) use of a compound of the formula (I) or a salt thereof for the manufacture of a pharmaceutical composition for preventing and/or treating cognitive impairment, negative symptoms of schizophrenia, Parkinson's disease, Alzheimer's disease, Huntington's disease, and drug addictions;
(2) use of a compound of the formula (I) or a salt thereof for preventing and/or treating cognitive impairment, negative symptoms of schizophrenia, Parkinson's disease, Alzheimer's disease, Huntington's disease, and drug addictions;
(3) a compound of the formula (I) or a salt thereof for preventing and/or treating cognitive impairment, negative symptoms of schizophrenia, Parkinson's disease, Alzheimer's disease, Huntington's disease, and drug addictions; and
(4) a method for preventing and/or treating cognitive impairment, negative symptoms of schizophrenia, Parkinson's disease, Alzheimer's disease, Huntington's disease, and drug addictions, which comprises administering to a subject an effective amount of a compound of the formula (I) or a salt thereof.

In this regard, the "subject" refers to a human or other animal in need of the prevention or treatment, and in a certain embodiment, a human in need of the prevention or treatment.

Effects of the Invention

A compound of the formula (I) or a salt thereof has a dopamine D1 receptor positive allosteric modulating activity, and can be used as an agent for preventing and/or treating cognitive impairment, negative symptoms of schizophrenia, Parkinson's disease, Alzheimer's disease, Huntington's disease, drug addictions, or the like.

EMBODIMENTS FOR CARRYING OUT THE INVENTION

Hereinafter, the present invention will be described in detail. In the definition of the present specification, "alkyl" and "alkylene" mean saturated, linear or branched hydrocarbon chains.

The "lower alkyl" is alkyl having 1 to 6 carbon atoms (hereinafter also referred to as $C_{1-6}$), for example, methyl, ethyl, n-propyl, isopropyl, n-butyl, isobutyl, sec-butyl, tert-butyl, n-pentyl, n-hexyl, or the like; in another embodiment, $C_{1-4}$ alkyl; in still another embodiment, methyl or ethyl; and in further still another embodiment, methyl.

The "lower alkylene" is $C_{1-6}$ alkylene, for example, methylene, ethylene, trimethylene, tetramethylene, pentamethylene, hexamethylene, propylene, methylmethylene, ethylethylene, 1,2-dimethylethylene, 2,2-dimethylethylene, 1,1,2,2-tetramethylethylene, or the like; in another embodiment, $C_{1-4}$ alkylene; in still another embodiment, ethylene, or 2,2-dimethylethylene; and in further still another embodiment, ethylene.

The "halogen" means F, Cl, Br, or I.

The "halogeno-lower alkyl" is $C_{1-6}$ alkyl substituted with one or more halogen atoms; in another embodiment, $C_{1-6}$ alkyl substituted with 1 to 5 halogen atoms; and in still another embodiment, $CF_3$.

The "cycloalkyl" is a $C_{3-10}$ saturated hydrocarbon ring group, which may have a bridge, for example, cyclopropyl, cyclobutyl, cyclopentyl, cyclohexyl, cycloheptyl, cyclooctyl, adamantyl, or the like; in another embodiment, $C_{3-6}$ cycloalkyl; and in still another embodiment, cyclopropyl.

Embodiments of the present invention are shown below.
(1) The compound or a salt thereof, in which in the formula (I), $R^1$ is halogen, halogeno-lower alkyl, or —O-halogeno-lower alkyl; in another embodiment, the compound or a salt thereof, in which $R^1$ is halogen or halogeno-lower alkyl; in still another embodiment, the compound or a salt thereof, in which $R^1$ is halogen; in further still another embodiment, the compound or a salt thereof, in which $R^1$ is Cl; in further still another embodiment, the compound or a salt thereof, in which $R^1$ is halogeno-lower alkyl; in further still another embodiment, the compound or a salt thereof, in which $R^1$ is $CF_3$; and in further still another embodiment, the compound or a salt thereof, in which $R^1$ is $OCF_3$.
(2) The compound or a salt thereof, in which in the formula (I), $R^2$ is H or F; in another embodiment, the compound or a salt thereof, in which $R^2$ is H; in still another embodiment, the compound or a salt thereof, in which $R^2$ is halogen; and in further still another embodiment, the compound or a salt thereof, in which $R^2$ is F.
(3) The compound or a salt thereof, in which in the formula (I), $R^{11}$, $R^{12}$, $R^{13}$ and $R^{14}$ are the same as or different from each other, and are H, halogen, halogeno-lower alkyl, cycloalkyl, or —O-halogeno-lower alkyl; in another embodiment, the compound or a salt thereof, in which $R^{11}$, $R^{12}$, $R^{13}$ and $R^{14}$ are the same as or different from each other, and are H, halogen, or halogeno-lower alkyl; in still another embodiment, the compound or a salt thereof, in which $R^{11}$, $R^{12}$, $R^{13}$ and R$^{14}$ are the same as or different from each other, and are H or halogeno-lower alkyl; in further still another embodiment, the compound or a salt thereof, in which R$^{12}$ is halogen or halogeno-lower alkyl, and R$^{11}$, R$^{13}$ and R$^{14}$ are H; in further still another embodiment, the compound or a salt thereof, in which R$^{12}$ is halogeno-lower alkyl, and R$^{11}$, R$^{13}$ and R$^{14}$ are H; in further still another embodiment, the compound or a salt thereof, in which R$^{12}$ is halogen, and R$^{11}$, R$^{13}$ and R$^{14}$ are H; in further still another embodiment, the compound or a salt thereof, in which R$^{12}$ is halogen or CF$_3$, and R$^{11}$, R$^{13}$ and R$^{14}$ are H; and in further still another embodiment, the compound or a salt thereof, in which R$^{12}$ is CF$_3$, and R$^{11}$, R$^{13}$ and R$^{14}$ are H.

(4) The compound or a salt thereof, in which in the formula (I), U is NR$^{15}$ and V is N.

(5) The compound or a salt thereof, in which in the formula (I), R$^{15}$ is H or -lower alkylene-OH; in another embodiment, the compound or a salt thereof, in which R$^{15}$ is H; and in still another embodiment, the compound or a salt thereof, in which R$^{15}$ is -lower alkylene-OH.

(6) The compound or a salt thereof, including a combination of two or more of the groups described in (1) to (5) in the formula (I).

Examples of the compound which is a combination of embodiments in (6) include the following.

(7) The compound or a salt thereof, in which in the formula (I), R$^1$ is halogen, halogeno-lower alkyl, or —O-halogeno-lower alkyl, and R$^{11}$, R$^{12}$, R$^{13}$ and R$^{14}$ are each the same as or different from each other, and are H, halogen, halogeno-lower alkyl, cycloalkyl, or —O-halogeno-lower alkyl.

(8) The compound or a salt thereof in (7), in which R$^{15}$ is H or -lower alkylene-OH.

(9) The compound or a salt thereof in (8), in which R$^1$ is halogen or halogeno-lower alkyl.

(10) The compound or a salt thereof in (9), in which R$^{11}$, R$^{12}$, R$^{13}$ and R$^{14}$ are the same as or different from each other, and are H, halogen, or halogeno-lower alkyl.

(11) The compound or a salt thereof in (10), in which R$^{12}$ is halogen or halogeno-lower alkyl, and R$^{11}$, R$^{13}$ and R$^{14}$ are H.

(12) The compound or a salt thereof in (10), in which R$^{12}$ is halogeno-lower alkyl, and R$^{11}$, R$^{13}$ and R$^{14}$ are H.

(13) The compound or a salt thereof in (10), in which R$^{12}$ is halogen, and R$^{11}$, R$^{13}$ and R$^{14}$ are H.

(14) The compound or a salt thereof in (10), in which R$^{12}$ is halogen or CF$_3$, and R$^{11}$, R$^{13}$ and R$^{14}$ are H.

(15) The compound or a salt thereof in (10), in which R$^{12}$ is CF$_3$, and R$^{11}$, R$^{13}$ and R$^{14}$ are H.

(16) The compound or salt thereof, in which in the formula (I), R$^1$ is halogen, R$^2$ is H, R$^{12}$ is halogeno-lower alkyl, R$^{11}$, R$^{13}$ and R$^{14}$ are H, U is NR$^{15}$, V is N, and R$^{15}$ is H.

(17) The compound or a salt thereof, in which in the formula (I), R$^1$ is halogen, R$^2$ is halogen, R$^{12}$ is halogeno-lower alkyl, R$^{11}$, R$^{13}$ and R$^{14}$ are H, U is NR$^{15}$, V is N, and R$^{15}$ is H.

(18) The compound or a salt thereof, in which in the formula (I), R$^1$ is halogen, R$^2$ is H, R$^{12}$ is halogen, R$^{11}$, R$^{13}$ and R$^{14}$ are H, U is NR$^{15}$, V is N, and R$^{15}$ is H.

Examples of the specific compounds included in the present invention include the following compounds and salts thereof:
2-(5-chloro-2-oxo-1,3-benzoxazol-3 (2H)-yl)-N-methyl-N-{[5-(trifluoromethyl)-1H-benzimidazol-2-yl]methyl}acetamide,
N-[(5-chloro-1H-benzimidazol-2-yl)methyl]-2-(5-chloro-2-oxo-1,3-benzoxazol-3 (2H)-yl)-N-methylacetamide,
2-(5-chloro-4-fluoro-2-oxo-1,3-benzoxazol-3(2H)-yl)-N-methyl-N-{[5-(trifluoromethyl)-1H-benzimidazol-2-yl]methyl}acetamide,
N-[(5-bromo-1H-benzimidazol-2-yl)methyl]-2-(5-chloro-2-oxo-1,3-benzoxazol-3(2H)-yl)-N-methylacetamide, or
N-[(5-chloro-1H-benzimidazol-2-yl)methyl]-N-methyl-2-[2-oxo-5-(trifluoromethyl)-1,3-benzoxazol-3(2H)-yl]acetamide Other embodiments of examples of the specific compounds included in the present invention include the following compounds:
2-(5-chloro-2-oxo-1,3-benzoxazol-3 (2H)-yl)-N-methyl-N-{[5-(trifluoromethyl)-1H-benzimidazol-2-yl]methyl}acetamide hydrochloride,
2-(5-chloro-4-fluoro-2-oxo-1,3-benzoxazol-3(2H)-yl)-N-methyl-N-{[5-(trifluoromethyl)-1H-benzimidazol-2-yl]methyl}acetamide, or
N-[(5-bromo-1H-benzimidazol-2-yl)methyl]-2-(5-chloro-2-oxo-1,3-benzoxazol-3 (2H)-yl)-N-methylacetamide.

The compound of the formula (I) may exist in the form of tautomers or geometrical isomers depending on the kind of substituents. In the present specification, the compound of the formula (I) shall be described in only one isomer form, yet the present invention includes any other isomers, isolated forms of the isomers, or a mixture thereof.

In addition, the compound of the formula (I) may have asymmetric carbon atoms in some cases, and correspondingly, it may exist in the form of optical isomers based thereon. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Molecular Design, 163-198.

Furthermore, the salt of the compound of the formula (I) may form an acid addition salt or a salt with a base depending on the kind of substituents, and such salts are included in the present invention as long as they are pharmaceutically acceptable salts. Specific examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid, and salts with inorganic bases such as sodium, potassium, magnesium, calcium, and aluminum, or organic bases such as methylamine, ethylamine, ethanolamine, lysine, and ornithine, salts with various amino acids such as acetylleucine, and amino acid derivatives, as well as ammonium salts.

In addition, the present invention also includes various hydrates or solvates, and polymorphic crystalline substances of the compound of the formula (I) and pharmaceutically acceptable salts thereof. In addition, the present invention also includes compounds labeled with various radioactive or non-radioactive isotopes.

The "positive allosteric modulating activity" means an activity that enhances the receptor function by binding to a site other than a site to which an endogenous ligand binds with respect to a receptor.

The "positive allosteric modulator" means a compound having a positive allosteric modulating activity. For example, in Test Example 1, it means a compound that shifts a dopamine dose-response curve leftward.

PAM does not enhance the receptor function in itself, but enhances the receptor function in the presence of a ligand.

Furthermore, the diseases in the present specification are named with reference to "ICD10" which is International Classification of Diseases of World Health Organization (WHO), 5th edition of the Diagnostic and Statistical Manual (DSM-5) of Mental Disorders in American Psychiatric Association (APA), and/or Societas Neurologica Japonica: Guideline.

The "schizophrenia" is a disease characterized by impairment of a variety of metal functions, such as cognition, emotion, motivation, behavior, and ego-consciousness. The symptoms thereof are classified into positive symptoms, negative symptoms, and cognitive impairments. The positive symptoms are, for example, symptoms such as hallucination and delusion. The negative symptoms are, for example, social withdrawal or emotional flattening. The cognitive impairments are, for example, formal thought disorder or working memory dysfunction.

In the present specification, the "negative symptoms of schizophrenia" means the negative symptoms in schizophrenia.

(Preparation Methods)

The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the relevant functional group) at the stage of starting materials or intermediates may be effective depending on the type of the functional group in the production technology in some cases. The protective group for such a functional group may include, for example, the protective groups described in "Greene's Protective Groups in Organic Synthesis (4th edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, prodrugs of the compound of the formula (I) can be prepared by introducing a specific group at the stage from a starting material to an intermediate or by carrying out the reaction using the obtained compound of the formula (I), just as in the case of the above-mentioned protective group. The reaction can be carried out using methods known to a person skilled in the art, such as ordinary esterification, amidation, dehydration, and the like.

Hereinbelow, representative preparation methods for the compound of the formula (I) will be described. Each production process may also be carried out with reference to the References appended in the present description. Further, the preparation methods of the present invention are not limited to the examples as shown below.

In the present specification, the following abbreviations may be used in some cases.

DMF=N,N-dimethylformamide, EtOAc=ethyl acetate, EtOH=ethanol, Hex=hexane, MeCN=acetonitrile, MeOH=methanol, THF=tetrahydrofuran.

nBuLi=n-butyllithium, CDI=1,1'-carbonylbis(1H-imidazole), DCC=N,N'-dicyclohexylcarbodiimide, DBU=1,8-diazabicyclo[5.4.0]undeca-7-ene, DIPEA=N,N-diisopropylethylamine, DMAP32N,N-dimethyl-4-aminopyridine, DMSO=dimethyl sulfoxide, DPPA=diphenylphosphoryl azide, HATU=O-(7-azabenzotriazol-1-yl)-N,N,N',N'-tetramethyluronium hexafluorophosphate, HOBt=1-hydroxybenzotriazole, KOtBu=potassium tert-butoxide, NMM=N-methyl morpholine, NMP32N-methyl-2-pyrrolidone, Pd/C=palladium-supported carbon, TEA=triethylamine, TFA=trifluoroacetic acid, WSC.HCl=N-[3-(dimethylamino)propyl]-N'-ethylcarbodiimide hydrochloride.

brine=a saturated aqueous NaCl solution, $MgSO_4$=anhydrous magnesium sulfate, $Na_2SO_4$=anhydrous sodium sulfate.

The following abbreviations may be used in some cases in the structural formulae or groups in the present specification.

Boc=tert-butoxycarbonyl, tBu=tert-butyl, Et=ethyl, Me=methyl, MOM=methoxymethyl, TBDMS=tert-butyldimethylsilyl.

(Production Process 1)

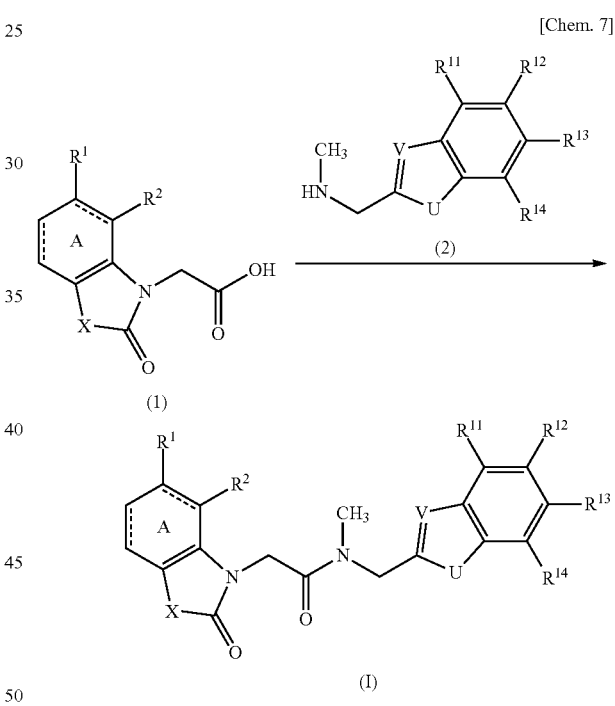

[Chem. 7]

The compound of the formula (I) can be prepared by amidation of a compound (1) and a compound (2).

In this reaction, the compound (1) and the compound (2) are used in equivalent amounts, or either thereof in an excess amount, and a mixture thereof is stirred in a range of from cooling to heating, preferably at a temperature from −20° C. to 60° C., usually for 0.1 hours to 5 days, in a solvent which is inert to the reaction, in the presence of a condensing agent. The solvent is not particularly limited, but examples thereof include aromatic hydrocarbons such as toluene or the like, halogenated hydrocarbons such as dichloromethane or the like, ethers such as THF or the like, DMF, NMP, DMSO, EtOAc, MeCN or water, and a mixture thereof. Examples of condensing agents include, but are not limited to, WSC.HCl, DCC, CDI, DPPA, and $POCl_3$. It may be preferable for the reaction to use an additive (for example, HOBt) in some cases. It is in some cases advantageous for smooth progress of the reaction to carry out the reaction in the presence of organic bases such as TEA, DIPEA, NMM or the like, or inorganic bases such as $K_2CO_3$, $Na_2CO_3$, KOH or the like.

Furthermore, it is also possible to use a method in which the compound (1) is converted to a reactive derivative thereof and then reacted with the compound (2). Examples of the reactive derivative of carboxylic acid include acid halides obtained by the reaction with a halogenating agent such as $POCl_3$, $SOCl_2$, and $(COCl)_2$ or the like, mixed acid anhydrides obtained by the reaction with isobutyl chloroformate or the like, and active esters obtained by condensation with HOBt or the like. A base such as DMAP or the like can be used as an additive. The reaction of these reactive derivatives with the compound (2) can be carried out in a range of from cooling to heating, and preferably from −78° C. to 60° C., in a solvent which is inert to the reaction, such as halogenated hydrocarbons, aromatic hydrocarbons, ethers or the like.

Further, examples of the references include "Organic Functional Group Preparations", S. R. Sandler and W. Karo, $2^{nd}$ edition, Vol. 1, Academic Press Inc., 1991, or The Chemical Society of Japan, "Courses in Experimental Chemistry, $5^{th}$ edition (Vol. 16)", Maruzen, 2005.

(Production Process 2)

[Chem. 8]

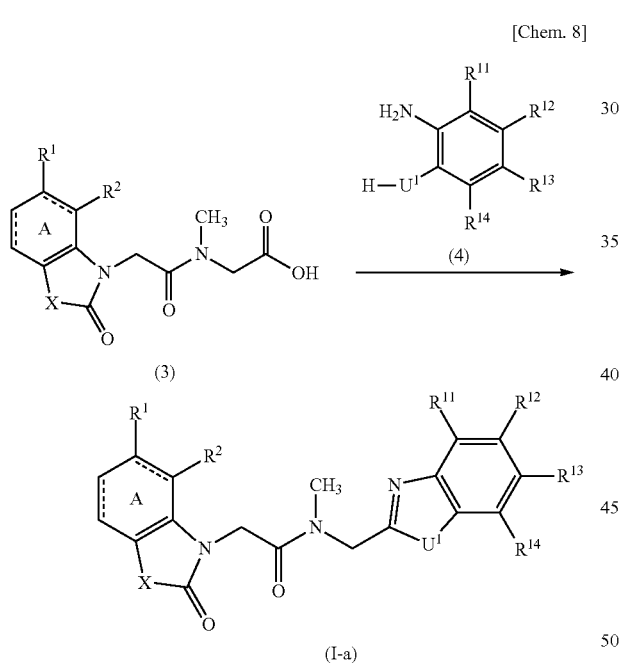

(in which $U^1$ represents NH or O, and the same shall apply hereinafter.)

A compound of the formula (I-a) can be prepared by amidation of a compound (3) and a compound (4), followed by a cyclization reaction. The reaction condition for amidation is the same as in Production Process 1. The cyclization reaction can be carried out by stirring under heating in a solvent such as aromatic hydrocarbons or without a solvent, in the presence of an acid such as acetic acid, hydrochloric acid, sulfuric acid, p-toluenesulfonic acid or the like.

(Preparation of Starting Compound)

In the preparation methods above, a starting compound can be prepared by using, for example, the methods below, the methods described in Preparation Examples as described later, known methods, or modified methods thereof.

(Starting Material Synthesis 1)

[Chem. 9]

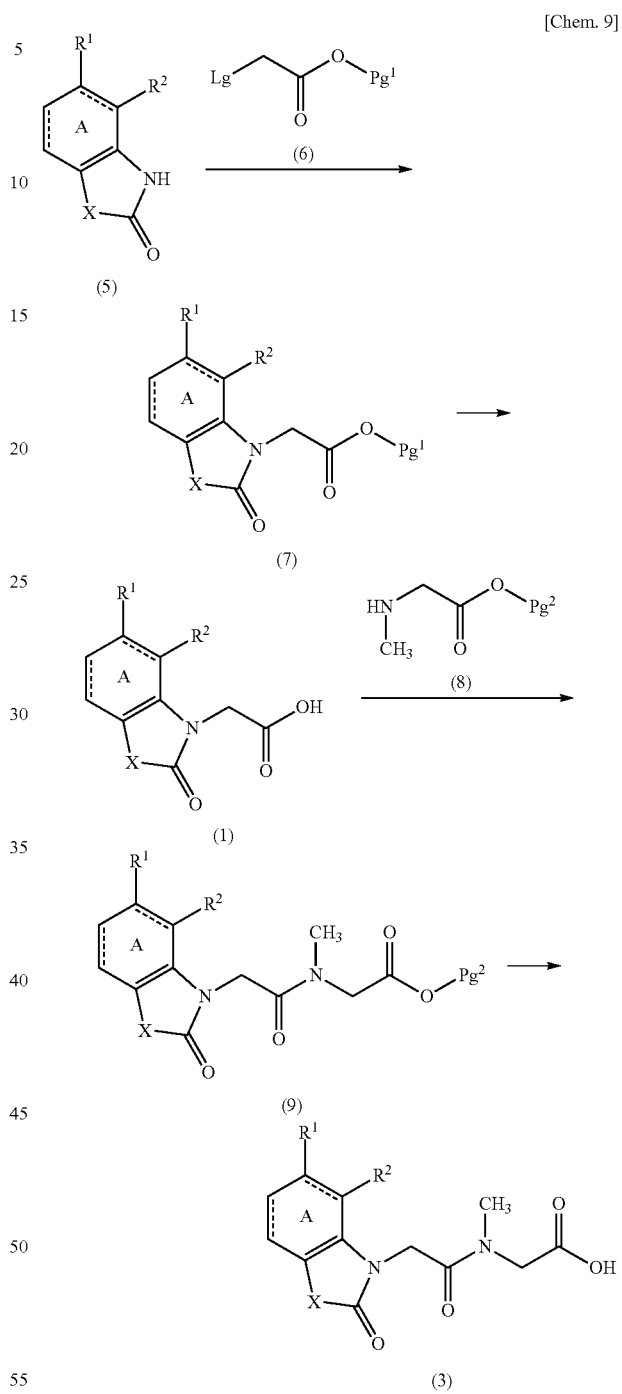

(in which Lg represents a leaving group, $Pg^1$ and $Pg^2$ represent a protective group, and the same shall apply hereinafter).

The compound (3) can be prepared by using a compound (5) as a starting material.

A compound (7) can be prepared from the compound (5) and a compound (6). Examples of the leaving group include halogen, a methanesulfonyloxy group, a p-toluenesulfonyloxy group and the like. Examples of the protective group include an Me group, an Et group, a tBu group and the like. In this reaction, the compound (5) and the compound (6) are used in equivalent amounts, or either thereof in an excess amount, and a mixture thereof is stirred in a range of from cooling to heating to reflux, preferably at a temperature from 0° C. to 80° C., usually for 0.1 hours to 5 days, in a solvent which is inert to the reaction, in the presence of a base. The solvent is not particularly limited, but examples thereof include aromatic hydrocarbons such as toluene or the like, ethers such as THF or the like, halogenated hydrocarbons such as dichloromethane or the like, DMF, DMSO, EtOAc, MeCN, and acetone, and a mixture thereof. Examples of base include organic bases such as TEA, DIPEA, DBU, nBuLi or the like, and inorganic bases such as $K_2CO_3$, $Na_2CO_3$, NaH, KOtBu or the like. It may be advantageous in some cases to carry out the reaction in the presence of a phase transfer catalyst such as tetra-n-butylammonium chloride.

The compound (1) can be prepared by deprotecting the compound (7). The deprotection may be carried out with reference to, for example, "Greene's Protective Groups in Organic Synthesis", 4th edition, 2006.

A compound (9) can be prepared by amidation of the compound (1) and a compound (8). For this reaction, the same condition as in Production Process 1 may be used.

The compound (3) can be prepared by deprotecting the compound (9).

(Starting Material Synthesis 2)

A compound (11) can be prepared by amidation of the compound (10) and a compound (4a), followed by a cyclization reaction. The reaction condition for amidation is the same as in Production Process 1.

For the cyclization reaction, the product can be prepared by stirring at 50° C. to 90° C. for 1 hour to 5 days, using an acid such as acetic acid or the like as a solvent. Examples of the protective group include any group with which the compound (11) or the compound (2a) is not cleaved in itself as well as under the reaction conditions above, and are not particularly limited. However, examples thereof include a Boc group and the like.

The compound (2a) can be prepared by deprotecting the compound (11).

(Starting Material Synthesis 3)

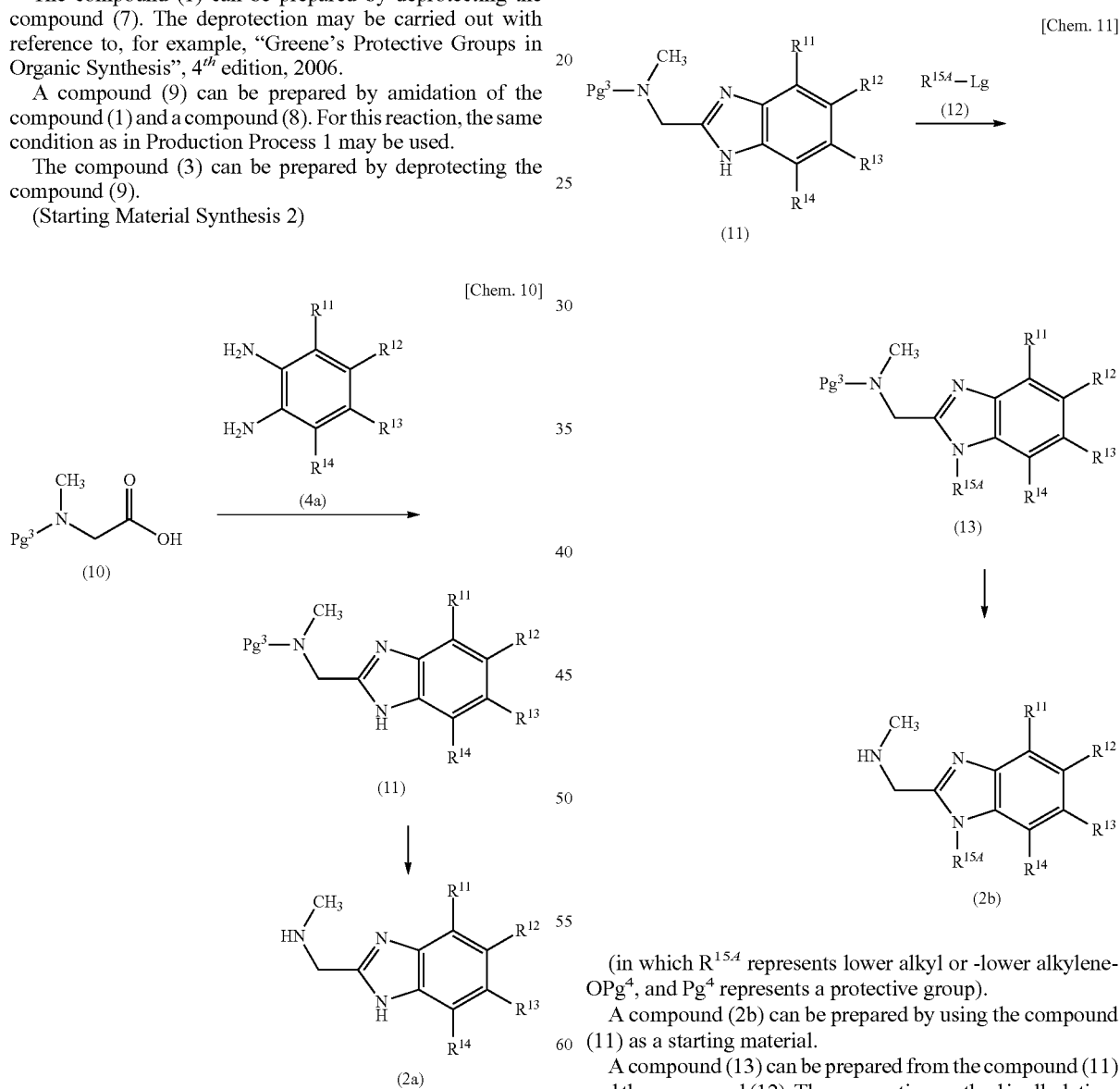

(in which $Pg^3$ represents a protective group, and the same shall apply hereinafter).

A compound (2a) can be prepared by using the compound (10) as a starting material.

(in which $R^{15A}$ represents lower alkyl or -lower alkylene-$OPg^4$, and $Pg^4$ represents a protective group).

A compound (2b) can be prepared by using the compound (11) as a starting material.

A compound (13) can be prepared from the compound (11) and the compound (12). The preparation method is alkylation, and can be conducted in the same manner as in the preparation method for the compound (7) from the compound (5) and the compound (6) in Starting Material Synthesis 1.

The compound (2b) can be prepared by deprotecting the compound (13).

(Starting Material Synthesis 4)

[Chem. 12]

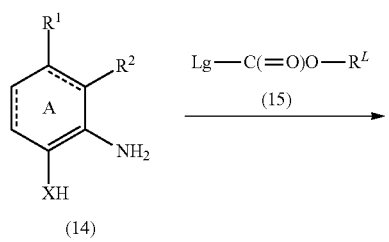

(in which $R^L$ represents lower alkyl.)

The compound (5) can be prepared by using a compound (14) as a starting material.

A compound (16) can be prepared by carbamation of a compound (14) and a compound (15). In this reaction, the compound (14) is stirred with the compound (15) at room temperature, in a range of room temperature to heating, or under heating to reflux for 0.1 hours to 10 hours, in a solvent which is inert to the reaction, such as dichloromethane or the like, in the presence of a base such as TEA, DIPEA, pyridine, NMM or the like.

The compound (5) can be prepared by a cyclization reaction of the compound (16). In this reaction, the compound (16) is stirred at 50° C. to 150° C., usually for 0.1 hours to 5 days, in a solvent which is inert to the reaction, such as DMF or the like, in the presence of an inorganic base such as $K_2CO_3$, $Na_2CO_3$, KOH or the like.

The compounds of the formula (I) are isolated and purified as free compounds, salts, hydrates, solvates, or polymorphic crystal polymorph thereof. Salts of the compound of the formula (I) can be prepared by conventional salt forming reactions.

Isolation and purification are carried out by employing ordinary chemical operations such as extraction, fractional crystallization, and fractional chromatography, and the like.

The compound of the formula (I) may exist in some cases as optical isomers based on the asymmetric carbon, depending on the kind of the substituent. Various isomers in the present invention can be prepared by selecting appropriate starting compounds or by separation using the difference in physicochemical properties between the isomers. For example, optical isomers can be obtained by means of a general optical resolution method for racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

(Abbreviated Symbols)

In the Test Examples in the present specification, the following abbreviations may be used in some cases.

ATCC=American Type Culture Collection, CHO cells=ovary cells of Chinese hamster, FBS=fetal bovine serum, IBMX=3-isobutyl-1-methylxanthine, MTX methotrexate, αMEM=Alpha modified Eagle's minimum essential medium which is ribonucleotide-free and contains L-alanyl and L-glutamine, NMDA=N-methyl-D-aspartic acid (Materials)

The composition of a buffer used in Test Example 1 is as follows.

Buffer for assay=αMEM containing 1 μM IBMX.

Buffer for dilution=αMEM containing 1 μM IBMX and 0.8 mM ascorbic acid.

Test Example 1

Evaluation of Positive Allosteric Modulating Activity

The positive allosteric modulating activity of the compound of the present invention was evaluated according to the ratio of the leftward shift in a dopamine dose-response curve.

The leftward shift means that a dose-response curve of dopamine, in which the logarithm of a dose is on the horizontal axis (X-axis) and a response (cAMP concentration in this test) is on the vertical axis (Y-axis), shifts in parallel in the negative direction of the X-axis by the administration of a positive allosteric modulator.

(Construction of Cells Stably Expressing Dopamine D1 Receptor in Human)

The coding sequences of a dopamine D1 receptor in a human (Accession No.: NM_000794.3) were amplified by PCR and subcloned into a pEF-BOS vector. The resulting construct was transfected to CHO (-dhrf) cells (ATCC No.: CRL-9096) using Lipofectamine 2000 (Invitrogen Inc.). The clones stably transfected were obtained by selection using 100 nM MTX. The obtained cell clones were maintained in αMEM containing 10% FBS, 1 mg/mL penicillin, and 1 U/streptomycin.

(Test Method)

(1) Dose-Response Curve of Dopamine Using Compound of the Present Invention

Dose-Response Curve of Dopamine Using test drug was drawn on the basis of the following experiments.

A buffer for assay of a test drug was serially diluted (concentrations 0.48 μM to 40 μM, 3-fold dilutions). The serially diluted solutions of the test drug were dispensed in each portion of 2.5 μL to black 384-well plates (Becton Dickinson, Inc.).

CHO cells stably expressing a dopamine D1 receptor of a human were seeded in each portion of 5 μL in each well at a density of 5000 cells/well, centrifuged in a centrifuge for a plate (05PR-22, Hitachi Co., Ltd., 800 rpm), and then allowed to stand for 10 minutes.

Serially diluted solutions of dopamine were prepared from a DMSO solution of dopamine (Sigma Co.) with a buffer for dilutions (concentrations 0.018 μM to 13.2 μM, 3-fold dilutions), and the serially diluted solutions of dopamine were dispensed in portions of 2.5 μL to each well of a plate.

The plate was stirred using a plate shaker (Sanko Junyaku (mx-5)) and then allowed to stand at room temperature for 20 minutes (final concentration: test drug 0 μM to 10 μM, dopamine 0 μM to 3.3 μM, 3-fold dilutions).

cAMP was quantified using a cAMP femto 2 kit (Sceti Medical Labo K. K.) by the method described in the materials appended in the kit. A kit reagent cAMP-d2 solution and a kit reagent Anti cAMP-Cryptate solution were added in each portion of 5 μL to each well of the above-described plate, and the reaction was stopped. After incubating the plate at room temperature for 1 hour, the fluorescent intensity was measured (an excitation wavelength of 320 nm and a fluorescent wavelength of 665 nm) using a plate reader (2103 Multilabel Reader (registered trademark EnVision), PerkinElmer, Inc.).

As a control group, a well without addition of dopamine was taken as 0% and a well with a dopamine final concentration of 3.3 μM was taken as 100%.

(2) Dose-Response Curve of Dopamine

The dose-response curve of dopamine was drawn on the basis of the experiment carried out in the same manner as in (1) without the addition of a test drug.

(Data Analysis)

As a result of the test, it was found that the dose-response curve (1) of dopamine with the addition of the compound of the present invention had a leftward shift with respect to the dose-response curve (2) of dopamine. The dose-response curve (1) of dopamine had an increased ratio of the leftward shift when the concentration of the compound of the present invention was increased.

In addition, in the case where the dopamine dose was 0, an agonistic action was not exhibited even when the compound of the present invention was added.

Accordingly, it was found that the compound of the present invention has a positive allosteric modulating activity.

In order to quantitatively compare the activity of the test drug, the activity was evaluated by $EC_{50}$ 2-fold potentiation.

In the present specification, "$EC_{50}$ 2-fold potentiation" is the test drug concentrations that enhanced the $EC_{50}$ two-fold in the dose-response curve (2) of dopamine.

From the dose-response curve (1) of dopamine in the presence of the test drug at each concentration, the $EC_{50}$ at the test drug concentration was obtained. From the correlation between the concentration of the test drug and the $EC_{50}$, $EC_{50}$ 2-fold potentiation was calculated by extrapolation by a linear function (straight line).

Further, the $EC_{50}$ value was calculated from the dose-response curves (1) and (2) of dopamine, using non-linear regression analysis.

For example, in the case where the $EC_{50}$ in the dose-response curve (2) of dopamine was 0.064 μM, the test drug concentration at which the $EC_{50}$ extrapolated from a linear function of the $EC_{50}$ in the dose-response curve (1) of dopamine in the presence of the test drug at each concentration and the test drug concentrations was 0.032 μM was taken as $EC_{50}$ 2-fold potentiation.

The results of some representative Example compounds in the present invention are shown in Table 1. In the Table, Ex represents Example compound No., and Data 1 represents an active index as defined above ($EC_{50}$ 2-fold potentiation, μM).

TABLE 1

| Ex | Data1 |
| --- | --- |
| 1 | 0.46 |
| 7 | 0.10 |
| 12 | 1.0 |
| 14 | 1.7 |
| 15 | 0.74 |
| 16 | 0.62 |
| 17 | 0.47 |
| 20 | 0.44 |
| 22 | 0.39 |
| 25 | 0.45 |
| 26 | 0.37 |
| 27 | 0.46 |

TABLE 1-continued

| Ex | Data1 |
| --- | --- |
| 30 | 0.27 |
| 31 | 1.1 |
| 34 | 0.99 |
| 37 | 0.30 |
| 39 | 0.40 |

Test Example 2

Y-Maze Test: Improvement Effect on Cognitive Impairment

The improvement effect of the compound of the present invention on cognitive impairment was evaluated using a Y-maze test which is an experiment system of alternation behavior.

(Experiment Device)

As a Y-maze, a maze, in which three tracks having a length of one arm of 40 cm, a height of a wall of 13 cm, a width of a bottom of 3 cm, and a width of a top of 10 cm are each joined in the Y shape at a degree of 120, was used.

(Test Method)

A test drug was orally administered once to a 5- to 6-week ddY male mice (n=8) at one hour before the Y maze test started, and further, MK-801 (Sigma Co.), which is an NMDA receptor antagonist causing cognitive impairment, had been intraperitoneally administered at a dose of 0.15 mg/kg at 20 minutes before the Y-maze test started.

Further, for the mice in a control group, a vehicle (0.5% methyl cellulose) was used instead of a test drug, and physiological saline, not MK-801, was used.

For the mice in the MK-801 control group, a vehicle (0.5% methyl cellulose) was used instead of the test drug.

The above-described mice were allowed to explore freely for 8 minutes after being placed at an end of one track in the Y-maze, and the track and the sequence in which the mice entered were recorded. The number of times the mice entered within the measurement time was counted, and taken as a total entry number. Among these, a combination in which the mice successively entered different three tracks (for example, when taking three arms as a, b, and c, respectively, a case where the order of the arm that entered was "abccbacab" was counted as 4, inclusive of overlapping) was considered as a spontaneous alternation behavior number. The spontaneous alternation behavior rate was calculated by the following calculation and used as an index for a spontaneous alternation behavior:

Spontaneous alternation behavior rate=spontaneous alternation behavior number/(total number of entries−2)×100

A higher index value indicates the maintenance of short-term memory.

(Data Analysis)

The measured values were expressed in average values±standard errors for each group. An assay for significant difference between the control group and the MK-801 control group was performed by a Student's t-test. Further, an assay for significant difference between the test drug-administered group and the MK-801 control group was performed by a Dunnett type multiple comparison assay, and an improvement effect of the test drug for learning disorder was determined. With P<0.05 in each assay, it was determined that there is a significant difference.

The results that some representative Example compounds of the present invention improved the spontaneous alternation behavior are shown in Table below. In the Table, Ex represents an Example compound No. Data 2 represents an effective concentration.

TABLE 2

| Ex | Data 2 | Ex | Data 2 |
|----|--------|----|--------|
| 1 | 0.1 mg/kg | 20 | 1.0 mg/kg |

As seen from the results of the tests above, the compound of the present invention can be used for, for example, preventing and/or treating cognitive impairment, negative symptoms of schizophrenia, Parkinson's disease, Alzheimer's disease, Huntington's disease, and drug addictions.

Pharmaceutical compositions containing one or more kinds of compound of formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal solutions, ointments, transdermal patches, transmucosal solutions, transmucosal patches, inhalers, and the like.

Solid compositions for oral administration are used in the form of tablets, powders, granules, or the like. In such solid compositions, one or more active ingredient(s) are mixed with at least one inactive excipient. In a conventional method, the composition may contain inactive additives, such as lubricants, disintegrating agents, stabilizers, or solubilization assisting agents. If necessary, tablets or pills may be coated with sugar or s gastric- or enteric-soluble substances films.

Liquid compositions for oral administration comprises pharmaceutically acceptable emulsions, solutions, suspensions, syrups, elixirs, or the like, and also comprises generally used inert diluents, for example, purified water or ethanol (EtOH). In addition to the inert diluent, liquid compositions may also contain auxiliary agents, such as solubilization assisting agents, moistening agents, and suspending agents, sweeteners, flavors, aromatics, or antiseptics.

Injections for parenteral administration include sterile aqueous or non-aqueous solutions, suspensions, or emulsions. Aqueous solvents include, for example, distilled water for injection or physiological saline. Examples of non-aqueous solvents include alcohols such as ethanol. Such compositions may further contain tonicity agents, antiseptics, moistening agents, emulsifying agents, dispersing agents, stabilizers, or solubilization assisting agents. These are sterilized, for example, by filtration through bacteria retaining filter, blendings of bactericide, or irradiation. In addition, these can also be used by preparing sterile solid compositions, and dissolving or suspending in sterile water or sterile solvents for injection prior to its use.

Agents for external use includes ointments, plasters, creams, jellies, poultices, sprays, lotions, eye drops, eye ointments, and the like. The agents contain generally used ointment bases, lotion bases, aqueous or non-aqueous solutions, suspensions, emulsions, and the like.

As transmucosal agents such as inhalers, transnasal agents, and the like, those in the form of a solid, liquid, or semi-solid state are used, and can be prepared in accordance with conventionally known methods. For example, known excipients, and furthermore pH adjusting agents, antiseptics, surfactants, lubricants, stabilizers, thickening agents, or the like may be appropriately added thereto. For their administration, appropriate devices for inhalation or blowing can be used. For example, a compound may be administered alone or as a powder of formulated mixture, or as a solution or suspension in combination with pharmaceutically acceptable carriers, using a known device or sprayer, such as a measured administration inhalation device, and the like. Dry powder inhalers or the like may be for single or multiple administration use, and dry powder or powder-containing capsules may be used. Alternatively, these may be pressurized aerosol spray which uses appropriate ejection agents, for example, a suitable gas such as chlorofluoroalkane, hydrofluoroalkane, carbon dioxide, and the like.

For oral administration, daily dose is generally from about 0.001 to 100 mg/kg, preferably from 0.1 to 30 mg/kg, and more preferably from 0.1 to 10 mg/kg, per body weight, administered in one portion or in 2 to 4 separate portions. In the case of intravenous administration, daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. Doses are appropriately determined according to the individual according to the symptoms, age, gender, and the like.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of formula (I) or a salt thereof, as the active ingredient.

The compound of formula (I) can be used in combination with various therapeutic or prophylactic agents for the diseases for which the compound of formula (I) is considered to be effective, as described above. The combined preparation may be administered simultaneously, or separately and continuously, or at a desired time interval. The preparations to be administered simultaneously may be a mixture, or may be prepared individually.

Example

Hereinbelow, the preparation methods for the compound of the formula (I) will be described in more detail with reference to Examples. The present invention is not limited to the compounds described in Examples as described below. Further, the production processes for the starting compounds will be described in Preparation Examples. Further, the preparation method for the compound of the formula (I) is not limited to the preparation methods in specific Examples shown below, and the compound of formula (I) can also be prepared by using a combination of the preparation methods or a method apparent to a person skilled in the art.

Furthermore, the following abbreviations may be used in some cases in Examples, Preparation Examples, and Tables below.

PEx: Preparation Example No., Ex: Example No., Syn: Example No. prepared by the same method, PSyn: Preparation Example No. prepared by the same method, Str: Structural formula, DAT: Physicochemical data, APCI+: m/z values in APCI-MS (representing $(M+H)^+$ unless otherwise specified), APCI/ESI+: m/z values in APCI/ESI-MS (representing (M+H)+ unless otherwise specified), EI+: m/z values in EI-MS (representing (M)+ unless otherwise specified), ESI+: m/z values in ESI-MS (representing (M+H)+ unless otherwise specified), ESI−: m/z values in ESI-MS (representing (M−H)− unless otherwise specified), FAB+: m/z values in FAB-MS (representing (M+H)+ unless otherwise specified), NMR1: δ (ppm) in $^1$H NMR in DMSO-$d_6$.

For example, a description of "3+4" in Syn indicates that preparation is performed by the same method as in Example 3, and is subsequently prepared by the same method as in Example 4 by using the product of Example 3 as a starting material. For example, in Tables below, there is a description of PSyn24+1 in Syn of Ex. 16, indicating that Example 16 is prepared by the same method as in Preparation Example 24, and is subsequently prepared by the same method as in Example 1 by using the product of Example 24 as a starting material. Further, HCl in the structural formula represents hydrochloride and the numeral before HCl denotes a molar ratio. For example, HCl means hydrochloride and 2HCl means dihydrochloride.

Furthermore, for the sake of convenience, a concentration mol/L is expressed by M. For example, a 1 M aqueous NaOH solution means a 1 mol/L aqueous NaOH solution.

The powder X-ray diffraction is measured using RINT-TTRII (RIGAKU Co.) under the conditions of a tube: Cu, a tube current: 300 mA, a tube voltage, 50 kV, a sampling width: 0.02°, a scanning speed: 4°/min, a wavelength: 1.54056 angstroms, and a measurement diffraction angle (2θ): 2.5 to 40°.

Each crystal is characterized by a powder X-ray diffraction pattern, respectively, but for the powder X-ray diffraction, the crystal lattice spacing and the overall pattern are important in the identification of the crystal in terms of the nature of the data. Further, since the relative intensities vary to some degree, depending on the direction of crystal growth, the particle size, and the measurement condition, they should not be interpreted strictly.

Preparation Example 1

Under an argon atmosphere, to a mixture of 5-chloro-1,3-benzoxazol-2(3H)-one (50.0 g) and acetone (750 mL) were added $K_2CO_3$ (61.1 g) and tert-butyl bromoacetate (52.3 mL) at room temperature, followed by heating to reflux for 1.5 hours. The reaction mixture was filtered while hot, and washed with acetone. The filtrate and the washed solution were combined and concentrated under reduced pressure. The obtained solid was stirred with a mixed solvent of Hex/EtOAc (6/1) and collected by filtration, and further stirred with water and collected by filtration to obtain tert-butyl (5-chloro-2-oxo-1,3-benzoxazol-3(2H)-yl)acetate (81.1 g).

Preparation Example 2

To a mixture of tert-butyl (5-chloro-2-oxo-1,3-benzoxazol-3(2H)-yl)acetate (50 g) and dichloromethane (250 mL) was added TFA (67.4 mL), followed by stirring at room temperature overnight. The reaction mixture was concentrated under reduced pressure, and then to the residue was added water. The resulting solid was collected by filtration and then washed with water to obtain (5-chloro-2-oxo-1,3-benzoxazol-3(2H)-yl)acetic acid (38.5 g).

Preparation Example 3

To a mixture of 2-amino-3-fluorophenol (2.07 g) and dichloromethane (100 mL) were added TEA (2.29 mL) and methyl chloroformate (1.27 mL) under ice-cooling, followed by stirring at room temperature for 3 hours. The reaction mixture was ice-cooled, and 0.5 M hydrochloric acid solution was added thereto, followed by stirring for 10 minutes. Then, the organic layer was separated. The organic layer was washed with brine, dried over $Na_2SO_4$, and then concentrated under reduced pressure. The residue was purified by silica gel column chromatography (eluent: Hex/EtOAc=100/0-75/25) to obtain methyl (2-fluoro-6-hydroxyphenyl)carbamate (2.55 g).

Preparation Example 4

To a mixture of methyl (2-fluoro-6-hydroxyphenyl)carbamate (346 mg) and MeCN (30 mL) was added p-toluenesulfonic acid monohydrate (711 mg), followed by stirring at room temperature for 5 minutes. To the reaction mixture was added N-chlorosuccinimide (250 mg), followed by stirring at room temperature overnight. The reaction mixture was diluted with chloroform, and washed with a 10% aqueous sodium thiosulfate solution and brine in this order. The organic layer was dried over $Na_2SO_4$, and then concentrated under reduced pressure. The residue was purified by silica gel column chromatography (eluent: Hex/EtOAc=80/20-70/30) to obtain methyl (3-chloro-2-fluoro-6-hydroxyphenyl)carbamate (173 mg).

Preparation Example 5

To a mixture of methyl (3-chloro-2-fluoro-6-hydroxyphenyl)carbamate (173 mg) and DMF (1.5 mL) was added $K_2CO_3$ (218 mg), followed by heating and stirring at 120° C. for 20 minutes. The reaction mixture was cooled to room temperature, and then added to ice water. To the reaction mixture was added concentrated hydrochloric acid (263 µL) under ice-cooling, followed by stirring at the same temperature for 30 minutes. The resulting solid was collected by filtration and then washed with water to obtain 5-chloro-4-fluoro-1,3-benzoxazol-2(3H)-one (117 mg).

Preparation Example 8

Under a nitrogen gas flow, to a mixture of NaH (55% in oil, 515 mg) and DMF (5 mL) was added a mixture of 7-chloroquinoxalin-2(1H)-one (2.00 g) and DMF (35 mL) under ice-cooling, followed by stirring at room temperature for 30 minutes. The reaction mixture was ice-cooled and ethyl bromoacetate (1.3 mL) was added thereto, followed by stirring at room temperature for 7 hours. The reaction mixture was added to water, followed by extraction with EtOAc. The organic layer was washed with water and brine in this order, dried over $Na_2SO_4$, and then concentrated under reduced pressure. The residue was purified by silica gel column chromatography (eluent: chloroform/MeOH=100/0-98/2). The obtained solid was washed with Hex to obtain ethyl (7-chloro-2-oxoquinoxalin-1(2H)-yl)acetate (2.21 g).

Preparation Example 9

To a mixture of ethyl (7-chloro-2-oxoquinoxalin-1(2H)-yl)acetate (2.21 g) and THF (25 mL) was added a 1 M aqueous NaOH solution (9.0 mL) at room temperature, followed by stirring at the same temperature for 4 hours. The reaction mixture was acidified by the addition of 1 M hydrochloric acid solution and then concentrated under reduced pressure. To the residue was added water, followed by stirring and collecting by filtration. The obtained solid was washed with water to obtain (7-chloro-2-oxoquinoxalin-1(2H)-yl)acetic acid (1.83 g).

Preparation Example 10

To a mixture of 5-trifluoromethyl-1,3-benzoxazol-2(3H)-one (999 mg) and acetone (25 mL) were added $K_2CO_3$ (1.02 g) and ethyl bromoacetate (708 µL) at room temperature, followed by heating to reflux for 4 hours. The reaction mixture was filtered while hot, and washed with acetone. The filtrate and the washed solution were combined and concentrated under reduced pressure. The residue was purified by silica gel column chromatography (eluent: Hex/EtOAc=100/0-75/25) to obtain ethyl [2-oxo-5-(trifluoromethyl)-1,3-benzoxazol-3(2H)-yl]acetate (1.33 g).

Preparation Example 12

To a mixture of methyl (2-fluoro-6-hydroxyphenyl)carbamate (1.06 g) and MeCN (90 mL) was added p-toluenesulfonic acid monohydrate (1.09 g), followed by stirring at room temperature for 5 minutes. To the reaction mixture was added N-iodosuccinimide (1.29 g), followed by stirring at room temperature overnight. The reaction mixture was diluted with chloroform, and washed with a 10% aqueous sodium thiosulfate solution and brine in this order. The organic layer was dried over $Na_2SO_4$ and then concentrated under reduced pressure. The residue was purified by silica gel column chromatography (eluent: Hex/EtOAc=85/15-75/25) to obtain methyl (2-fluoro-6-hydroxy-3-iodophenyl)carbamate (408 mg).

Preparation Example 15

Under an argon atmosphere, to a mixture of tert-butyl (4-fluoro-5-iodo-2-oxo-1,3-benzoxazol-3(2H)-yl)acetate (400 mg) and DMF (15 mL) were added methyl 2,2-difluoro-2-(fluorosulfonyl)acetate (1.94 mL) and copper iodide (969 mg), followed by heating and stirring at 110° C. overnight. The reaction mixture was cooled to room temperature, and then the insoluble materials were separated by filtration over Celite, followed by washing with chloroform. The filtrate was washed with a saturated aqueous $NaHCO_3$ solution, dried over $Na_2SO_4$, and then concentrated under reduced pressure. The residue was purified by silica gel column chromatography (eluent: Hex/EtOAc=100/0-90/10) to obtain tert-butyl [4-fluoro-2-oxo-5-(trifluoromethyl)-1,3-benzoxazol-3(2H)-yl]acetate (296 mg).

Preparation Example 17

To a mixture of 2-amino-4-(trifluoromethoxy)phenol (1.01 g) and 1,4-dioxane (20 mL) was added CDI (1.10 g), followed by heating and stirring at 70° C. for 7 hours. The reaction mixture was cooled to room temperature, and then the solvent was concentrated to a half of the volume under reduced pressure. To the obtained residue was added water (30 mL), followed by adjusting to pH 4 by the addition of concentrated hydrochloric acid under ice-cooling, and stirring at the same temperature for 1 hour. The resulting solid was collected by filtration to obtain 5-(trifluoromethoxy)-1,3-benzoxazol-2 (3H)-one (830 mg).

Preparation Example 20

To a mixture of (5-chloro-2-oxo-1,3-benzothiazol-3(2H)-yl)acetic acid (200 mg), N-methylglycine ethyl ester hydrochloride (130 mg) and dichloromethane (5 mL) were added TEA (280 µL), HOBt (122 mg), and WSC.HCl (173 mg), followed by stirring at room temperature overnight. The reaction mixture was diluted with EtOAc. The organic layer was washed with water, a saturated aqueous $NaHCO_3$ solution, and brine in this order, dried over $Na_2SO_4$, and then concentrated under reduced pressure. The residue was purified by silica gel column chromatography (eluent: Hex/EtOAc=100/0-50/50).

To a mixture of the purified product thus obtained and EtOH (5 mL) was added a 1 M aqueous NaOH solution (900 µL), followed by stirring at room temperature for 3 hours. To the reaction mixture were added water and 1 M hydrochloric acid solution (900 µL), followed by extraction with chloroform. The organic layer was dried over $Na_2SO_4$ and then concentrated under reduced pressure to obtain N-[(5-chloro-2-oxo-1,3-benzothiazol-3(2H)-yl)acetyl]-N-methylglycine (188 mg).

Preparation Example 22

To a solution of 3-(trifluoromethyl)benzene-1,2-diamine (500 mg) and N-(tert-butoxycarbonyl)-N-methylglycine (537 mg) in DMF (5 mL) were added WSC.HCl (653 mg) and HOBt (384 mg), followed by stirring at room temperature overnight. The reaction mixture was diluted with EtOAc. The organic layer was washed with water, a saturated aqueous $NaHCO_3$ solution, and brine in this order, dried over $MgSO_4$, and then concentrated under reduced pressure. To the residue was added acetic acid (5 mL), followed by heating and stirring at 70° C. for 3 hours. The reaction mixture was concentrated under reduced pressure and diluted with EtOAc. The organic layer was washed with a saturated aqueous $NaHCO_3$ solution and brine in this order, dried over $MgSO_4$, and then concentrated under reduced pressure. The residue was purified by silica gel column chromatography (eluent: Hex/EtOAc=80/20-40/60) to obtain tert-butyl methyl {[4-(trifluoromethyl)-1H-benzimidazol-2-yl]methyl}carbamate (420 mg).

Preparation Example 23

To a mixture of N-(tert-butoxycarbonyl)-N-methylglycine (1.17 g) and THF (14 mL) were added TEA (1.4 mL) and isobutyl chloroformate (841 µL) under ice-cooling, followed by stirring at room temperature for 1 hour. The resulting solid was separated by filtration and washed with THF (10 mL). To the filtrate was added 4-(trifluoromethyl)benzene-1,2-diamine (1.10 g) under ice-cooling, followed by stirring at room temperature overnight. The reaction mixture was concentrated under reduced pressure. To the residue was added acetic acid (10 mL), followed by heating and stirring at 80° C. for 2.5 hours. The reaction mixture was cooled to room temperature and concentrated under reduced pressure. The residue was purified by silica gel column chromatography (eluent: Hex/EtOAc=80/20-40/60) to obtain tert-butyl methyl {[5-(trifluoromethyl)-1H-benzimidazol-2-yl]methyl}carbamate (1.89 g).

Preparation Example 24

To a mixture of tert-butyl methyl {[5-(trifluoromethyl)-1H-benzimidazol-2-yl]methyl}carbamate (1.89 g) and MeOH (18 mL) was added 4 M hydrogen chloride/EtOAc (8.6 mL), followed by heating and stirring at 50° C. for 3 hours. The reaction mixture was concentrated under reduced pressure. The resulting solid was collected by filtration and then washed with EtOAc to obtain N-methyl-1-[5-(trifluoromethyl)-1H-benzimidazol-2-yl]methanamine dihydrochloride (1.41 g).

Preparation Example 41

To a mixture of 4-ethoxy-2-nitroaniline (963 mg) and THF/EtOH (1/1, 10 mL) was added 10% Pd/C (281 mg), followed by stirring at room temperature for 3 hours under a hydrogen atmosphere. The reaction mixture was filtered and the filtrate was concentrated under reduced pressure to obtain 4-ethoxybenzene-1,2-diamine.

To a solution of N-(tert-butoxycarbonyl)-N-methylglycine (500 mg) in THF (5 mL) were added isobutyl chloroformate (380 µL) and DIPEA (498 µL) at 0° C., followed by stirring at room temperature for 1 hour. The resulting solid was separated by filtration and washed with THF. To this filtrate was added a solution of 4-ethoxybenzene-1,2-diamine obtained above in THF (5 mL), followed by stirring at room temperature overnight. To the reaction mixture was added a saturated aqueous $NaHCO_3$ solution, followed by extraction with EtOAc. The organic layer was washed with brine, dried over $MgSO_4$, and then concentrated under reduced pressure. The residue was purified by silica gel column chromatography (eluent: chloroform/MeOH=100/0-80/20).

To the purified product thus obtained was added acetic acid (5 mL), followed by heating and stirring at 80° C. for 3 hours, and then concentrating under reduced pressure. To the residue was added a saturated aqueous $NaHCO_3$ solution, followed by extraction with EtOAc. The organic layer was washed with brine, dried over $MgSO_4$, and then concentrated under reduced pressure. The residue was purified by silica gel column chromatography (eluent: chloroform/MeOH=100/0-80/20) to obtain tert-butyl [(5-ethoxy-1H-benzimidazol-2-yl)methyl]methylcarbamate (380 mg).

Preparation Example 42

To a mixture of 3-chloro-2-nitroaniline (684 mg) and EtOH (5 mL) were added ammonium chloride (353 mg) and water (1.5 mL), followed by adding zinc powder (1.38 g) at 80° C., and heating and stirring at 80° C. for 30 minutes. The reaction mixture was cooled to room temperature, filtered over Celite, and washed with EtOAc. This filtrate was washed with a saturated aqueous $NaHCO_3$ solution and brine in this order, dried over $MgSO_4$, and then concentrated under reduced pressure to obtain 3-chlorobenzene-1,2-diamine.

To a solution of N-(tert-butoxycarbonyl)-N-methylglycine (500 mg) in THF (5 mL) were added DIPEA (498 µL) and isobutyl chloroformate (363 µL) at 0° C., followed by stirring at room temperature for 1 hour. The resulting solid was separated by filtration and washed with THF. To this filtrate was added a solution of 3-chlorobenzene-1,2-diamine obtained above in THF (5 mL), followed by stirring overnight. The reaction mixture was diluted with EtOAc, washed with a saturated aqueous $NaHCO_3$ solution and brine in this order, dried over $MgSO_4$, and then concentrated under reduced pressure. To the residue was added acetic acid (5 mL), followed by heating and stirring at 80° C. overnight, and then concentrating under reduced pressure. To the residue was added a saturated aqueous $NaHCO_3$ solution, followed by extraction with chloroform. The organic layer was dried over $MgSO_4$ and then concentrated under reduced pressure. The residue was purified by silica gel column chromatography (eluent: Hex/EtOAc=60/40-0/100) to obtain tert-butyl [(4-chloro-1H-benzimidazol-2-yl)methyl]methylcarbamate (400 mg).

Preparation Example 43

To a mixture of 2-nitro-4-(trifluoromethoxy)aniline (1.17 g) and EtOH (20 mL) were added ammonium chloride (565 mg) and water (5 mL), followed by further adding zinc powder (1.73 g) at 60° C., and heating and stirring at 60° C. for 1 hour. The reaction mixture was cooled to room temperature, filtered over Celite, and washed with EtOAc. This filtrate was washed with a saturated aqueous $NaHCO_3$ solution and brine in this order, dried over $MgSO_4$, and then concentrated under reduced pressure to obtain 4-(trifluoromethoxy)benzene-1,2-diamine.

To a solution of N-(tert-butoxycarbonyl)-N-methylglycine (1.00 g) in THF (12 mL) were added TEA (1.2 mL) and isobutyl chloroformate (719 µL) at 0° C., followed by stirring at room temperature for 1 hour. The resulting solid was separated by filtration and washed with THF. To this filtrate was added a solution of 4-(trifluoromethoxy)benzene-1,2-diamine obtained above in THF (12 mL), followed by stirring overnight. The reaction mixture was diluted with EtOAc, washed with a saturated aqueous $NaHCO_3$ solution and brine in this order, dried over $MgSO_4$, and then concentrated under reduced pressure. To the residue was added acetic acid (8.5 mL), followed by heating and stirring at 80° C. overnight, and then concentrating under reduced pressure. The residue was diluted with EtOAc, washed with a saturated aqueous $NaHCO_3$ solution and brine in this order, dried over $MgSO_4$, and then concentrated under reduced pressure. The residue was purified by silica gel column chromatography (eluent: chloroform/MeOH=100/0-80/20).

To the purified product thus obtained was added 4 M hydrogen chloride/EtOAc (6.6 mL), followed by stirring at room temperature for 2 hours and then concentrating under reduced pressure to obtain N-methyl-1-[5-(trifluoromethoxy)-1H-benzimidazol-2-yl]methanamine dihydrochloride (50 mg).

Preparation Example 44

To a mixture of tert-butyl [(5-bromo-1H-benzimidazol-2-yl)methyl]methylcarbamate (1.54 g) and DMF (20 mL) were added $K_2CO_3$ (1.88 g) and chloromethylmethyl ether (516 µL) under ice-cooling, followed by stirring at room temperature overnight. The reaction mixture was diluted with EtOAc, and washed with water and brine in this order. The organic layer was dried over $Na_2SO_4$ and then concentrated under reduced pressure. The residue was purified by silica gel column chromatography (eluent: Hex/EtOAc=80/20-55/45) to obtain a mixture (1.25 g) of tert-butyl {[5-bromo-1-(methoxymethyl)-1H-benzimidazol-2-yl]methyl}methylcarbamate and tert-butyl {[6-bromo-1-(methoxymethyl)-1H-benzimidazol-2-yl]methyl}methylcarbamate.

Preparation Example 45

To a mixture of a mixture (1.25 g) of tert-butyl {[5-bromo-1-(methoxymethyl)-1H-benzimidazol-2-yl]methyl}methylcarbamate and tert-butyl {[6-bromo-1-(methoxymethyl)-1H-benzimidazol-2-yl]methyl}methylcarbamate and toluene/water (20/1, 26.3 mL) were added cyclopropylboronic acid (840 mg), palladium (II) acetate (146 mg), tricyclohexylphosphine (365 mg), and potassium phosphate (4.14 g), followed by heating and stirring at 100° C. overnight. The reaction mixture was diluted with EtOAc, and washed with water, 1 M hydrochloric acid solution, and brine in this order. The organic layer was dried over Na$_2$SO$_4$ and then concentrated under reduced pressure. The residue was purified by silica gel column chromatography (eluent: Hex/EtOAc=80/20-55/45) to obtain a mixture (505 mg) of tert-butyl {[5-cyclopropyl-1-(methoxymethyl)-1H-benzimidazol-2-yl]methyl}methylcarbamate and tert-butyl {[6-cyclopropyl-1-(methoxymethyl)-1H-benzimidazol-2-yl]methyl}methylcarbamate.

Preparation Example 46

To a mixture of a mixture (501 mg) of tert-butyl {[5-cyclopropyl-1-(methoxymethyl)-1H-benzimidazol-2-yl]methyl}methylcarbamate and tert-butyl {[6-cyclopropyl-1-(methoxymethyl)-1H-benzimidazol-2-yl]methyl}methylcarbamate and EtOH/water (1/1, 6 mL) was added 4 M hydrogen chloride/1,4-dioxane (6 mL), followed by heating and stirring at 80° C. for 5 hours and then concentrating under reduced pressure to obtain 1-(5-cyclopropyl-1H-benzimidazol-2-yl)-N-methylmethanamine dihydrochloride (328 mg).

Preparation Example 47

To a mixture of N-(tert-butoxycarbonyl)-N-methylglycine (1.00 g), 4-methoxybenzene-1,2-diamine dihydrochloride (1.16 g) and DMF (25 mL) were added HATU (2.41 g) and DIPEA (4.5 mL), followed by stirring at room temperature overnight. The reaction mixture was diluted with EtOAc, and washed with water and brine in this order. The organic layer was dried over Na$_2$SO$_4$ and then concentrated under reduced pressure. To the residue was added acetic acid (20 mL), followed by heating and stirring at 80° C. for 3 hours, and then concentrating under reduced pressure. The residue was purified by basic silica gel column chromatography (eluent: Hex/EtOAc=80/20-20/80) to obtain tert-butyl [(5-methoxy-1H-benzimidazol-2-yl)methyl]methylcarbamate (1.22 g).

Preparation Example 49

To a mixture of a mixture (946 mg) of tert-butyl {[5-methoxy-1-(methoxymethyl)-1H-benzimidazol-2-yl]methyl}methylcarbamate and tert-butyl {[6-methoxy-1-(methoxymethyl)-1H-benzimidazol-2-yl]methyl}methylcarbamate and dichloromethane (10 mL) was added N-bromosuccinimide (527 mg) under ice-cooling, followed by stirring at room temperature overnight. The reaction mixture was diluted with EtOAc, and washed with a saturated aqueous NaHCO$_3$ solution and brine in this order. The organic layer was dried over Na$_2$SO$_4$ and then concentrated under reduced pressure. The residue was purified by silica gel column chromatography (eluent: Hex/EtOAc=85/15-60/40) to obtain a mixture (855 mg) of tert-butyl {[6-bromo-5-methoxy-1-(methoxymethyl)-1H-benzimidazol-2-yl]methyl}methylcarbamate and tert-butyl {[5-bromo-6-methoxy-1-(methoxymethyl)-1H-benzimidazol-2-yl]methyl}methylcarbamate.

Preparation Example 51

To a mixture of tert-butyl [(5,6-dichloro-1H-benzimidazol-2-yl)methyl]methylcarbamate (400 mg) and DMF (4 mL) were added ethyl bromoacetate (201 μL) and K$_2$CO$_3$ (335 mg), followed by heating and stirring at 70° C. for 2 hours. The reaction mixture was diluted with EtOAc, washed with water and brine in this order, dried over MgSO$_4$, and then concentrated under reduced pressure. The residue was purified by silica gel column chromatography (eluent: Hex/EtOAc=50/50-0/100) to obtain ethyl (2-{[(tert-butoxycarbonyl)(methyl)amino]methyl}-5,6-dichloro-1H-benzimidazol-1-yl)acetate (393 mg).

Preparation Example 52

To a mixture of ethyl (2-{[(tert-butoxycarbonyl)(methyl)amino]methyl}-5,6-dichloro-1H-benzimidazol-1-yl)acetate (390 mg) and THF (8 mL) was added dropwise methylmagnesium bromide (3 M THF solution, 0.94 mL) at room temperature, followed by stirring at room temperature for 1 hour. To the reaction mixture was added water, followed by extraction with EtOAc. The organic layer was washed with brine, dried over MgSO$_4$, and then concentrated under reduced pressure. The residue was purified by silica gel column chromatography (eluent: Hex/EtOAc=70/30-40/60) to obtain tert-butyl {[5,6-dichloro-1-(2-hydroxy-2-methylpropyl)-1H-benzimidazol-2-yl]methyl}methylcarbamate (70 mg).

Preparation Example 53

To a mixture of (5-chloro-2-oxo-1,3-benzothiazol-3(2H)-yl)acetic acid (300 mg), 1-(5-chloro-1H-benzimidazol-2-yl)-N-methylmethanamine (265 mg) and DMF (20 mL) were added TEA (687 μL), HOBt (200 mg), and WSC.HCl (283 mg), followed by stirring at room temperature overnight. To the reaction mixture was added water, followed by extraction with EtOAc. The organic layer was washed with water, a saturated aqueous NaHCO$_3$ solution, and brine in this order, dried over Na$_2$SO$_4$, and then concentrated under reduced pressure. The obtained solid was washed with EtOAc to obtain N-[(5-chloro-1H-benzimidazol-2-yl)methyl]-2-(5-chloro-2-oxo-1,3-benzothiazol-3(2H)-yl)-N-methylacetamide (339 mg).

Preparation Example 55

To a mixture of 2-(5-chloro-2-oxo-1,3-benzoxazol-3(2H)-yl)-N-[(5,6-dichloro-1H-benzimidazol-2-yl)methyl]-N-methylacetamide (150 mg) and DMF (4.5 mL) were added K$_2$CO$_3$ (94 mg) and 1-bromo-2-(methoxymethoxy)ethane (80 μL), followed by heating and stirring at 70° C. for 5 hours. The reaction mixture was cooled to room temperature and then diluted with EtOAc. The organic layer was washed with water and brine in this order, dried over MgSO$_4$, and then concentrated under reduced pressure. The residue was purified by silica gel column chromatography (eluent: Hex/EtOAc=50/50-0/100) to obtain 2-(5-chloro-2-oxo-1,3-benzoxazol-3(2H)-yl)-N-({5,6-dichloro-1-[2-(methoxymethoxy)ethyl]-1H-benzimidazol-2-yl}methyl)-N-methylacetamide (110 mg).

Preparation Example 56

To a mixture of N-(1H-benzimidazol-2-ylmethyl)-2-(5-chloro-2-oxo-1,3-benzothiazol-3(2H)-yl)-N-methylacetamide (500 mg) and DMF (15 mL) were added (2-bromoethoxy)(tert-butyl)dimethylsilane (555 μL) and K$_2$CO$_3$ (358 mg), followed by heating and stirring at 95° C. for 24 hours. The reaction mixture was diluted with EtOAc, and washed with water and brine in this order. The organic layer was dried over Na$_2$SO$_4$ and then concentrated under reduced pressure. To the resulting solid was added EtOAc, followed by suspending. An equivalent amount of Hex was added thereto, followed by collecting by filtration and washing with a Hex-EtOAc mixed solvent to obtain N-{[1-(2-{[tert-butyl(dimethyl)silyl]oxy}ethyl)-1H-benzimidazol-2-yl]methyl}-2-(5-chloro-2-oxo-1,3-benzothiazol-3(2H)-yl)-N-methylacetamide (523 mg).

Example 1

To a mixture of (5-chloro-2-oxo-1,3-benzoxazol-3(2H)-yl)acetic acid (300 mg), N-methyl-1-[5-(trifluoromethyl)-1H-benzimidazol-2-yl]methanamine dihydrochloride (420 mg), and dichloromethane (10 mL) were added TEA (552 µL), HOBt (214 mg), and WSC.HCl (303 mg), followed by stirring at room temperature overnight. The reaction mixture was diluted with EtOAc. The organic layer was washed with water, a saturated aqueous NaHCO₃ solution, and brine in this order, dried over Na₂SO₄, and then concentrated under reduced pressure. The resulting solid was collected by filtration and washed with EtOAc. To a mixture of the obtained solid (325 mg) and MeOH (5 mL) was added 4 M hydrogen chloride/EtOAc (330 µL), followed by stirring at room temperature for 1 hour. To the reaction mixture was added EtOAc. The resulting solid was collected by filtration and then washed with EtOAc to obtain 2-(5-chloro-2-oxo-1,3-benzoxazol-3 (2H)-yl)-N-methyl-N-{[5-(trifluoromethyl)-1H-benzimidazol-2-yl]methyl}acetamide hydrochloride (277 mg).

Example 2

To a mixture of (5-chloro-2-oxo-1,3-benzothiazol-3(2H)-yl)acetic acid (731 mg), 1-(1H-benzimidazol-2-yl)-N-methylmethanamine dihydrochloride (736 mg), and dichloromethane (20 mL) were added HOBt (448 mg), WSC.HCl (633 mg), and TEA (1.05 mL), followed by stirring at room temperature overnight. The resulting solid was collected by filtration and then washed with chloroform to obtain N-(1H-benzimidazol-2-ylmethyl)-2-(5-chloro-2-oxo-1,3-benzothiazol-3(2H)-yl)-N-methylacetamide (925 mg).

Example 3

To a mixture of N-[(5-chloro-2-oxo-1,3-benzothiazol-3 (2H)-yl)acetyl]-N-methylglycine (90 mg), 4,5-dichlorobenzene-1,2-diamine (53 mg), and DMF (3 mL) were added TEA (95 µL), HOBt (43 mg), and WSC.HCl (60 mg), followed by stirring at room temperature overnight. The reaction mixture was diluted with EtOAc. The organic layer was washed with water, a saturated aqueous NaHCO₃ solution, and brine in this order, dried over Na₂SO₄, and then concentrated under reduced pressure. To the residue was added acetic acid (3 mL), followed by heating and stirring at 110° C. for 5 hours. The reaction mixture was cooled to room temperature and then concentrated under reduced pressure. The residue was diluted with EtOAc. The organic layer was washed with a saturated aqueous NaHCO₃ solution and brine in this order, dried over Na₂SO₄, and then concentrated under reduced pressure. The resulting solid was collected by filtration and then washed with MeOH to obtain 2-(5-chloro-2-oxo-1,3-benzothiazol-3(2H)-yl)-N-[(5,6-dichloro-1H-benzimidazol-2-yl)methyl]-N-methylacetamide (54 mg).

Example 4

To a mixture of N-[(5-chloro-2-oxo-1,3-benzothiazol-3 (2H)-yl)acetyl]-N-methylglycine (150 mg), 4-chloro-5-fluorobenzene-1,2-diamine (81 mg), and DMF (5 mL) were added HOBt (77 mg) and WSC.HCl (107 mg), followed by stirring at room temperature overnight. The reaction mixture was diluted with EtOAc, and washed with water, a saturated aqueous NaHCO₃ solution, and brine in this order, dried over Na₂SO₄, and then concentrated under reduced pressure. To the residue was added acetic acid (5 mL), followed by heating and stirring at 110° C. for 5 hours. The reaction mixture was cooled to room temperature and concentrated under reduced pressure. The residue was diluted with EtOAc. The organic layer was washed with a saturated aqueous NaHCO₃ solution and brine in this order, dried over Na₂SO₄, and then concentrated under reduced pressure. The obtained solid was washed with EtOAc and then with MeOH, and suspended in MeOH (3 mL). 4 M hydrogen chloride/EtOAc (120 µL) was added thereto, followed by stirring at room temperature for 1 hour. The resulting solid was collected by filtration and then washed with MeOH to obtain N-[(6-chloro-5-fluoro-1H-benzimidazol-2-yl)methyl]-2-(5-chloro-2-oxo-1,3-benzothiazol-3(2H)-yl)-N-methylacetamide hydrochloride (146 mg).

Example 5

To a mixture of N-[(5-chloro-2-oxo-1,3-benzothiazol-3 (2H)-yl)acetyl]-N-methylglycine (205 mg) and THF (5 mL) were added oxalyl chloride (78 µL) and a catalytic amount of DMF under ice-cooling, followed by stirring at room temperature for 2 hours. The reaction mixture was concentrated under reduced pressure. A mixture of the residue and dichloromethane (4 mL) was added to a mixture of 2-amino-4-chlorophenol (84 mg), TEA (91 µL), and dichloromethane (1 mL) under ice-cooling, followed by stirring at room temperature overnight. The reaction mixture was added to brine, followed by extraction with chloroform. The organic layer was dried over Na₂SO₄ and then concentrated under reduced pressure. To a mixture of the residue and toluene (5 mL) was added p-toluenesulfonic acid monohydrate (134 mg), followed by heating to reflux for 5 hours. The reaction mixture was cooled to room temperature, diluted with EtOAc, and washed with water, a saturated aqueous NaHCO₃ solution, and brine in this order. The organic layer was dried over Na₂SO₄ and then concentrated under reduced pressure. The residue was purified by silica gel column chromatography (eluent: Hex/EtOAc=85/15-50/50). To the purified product thus obtained was added diethyl ether. The resulting solid was collected by filtration and then washed with diethyl ether to obtain N-[(5-chloro-1,3-benzoxazol-2-yl)methyl]-2-(5-chloro-2-oxo-1,3-benzothiazol-3(2H)-yl)-N-methylacetamide (59 mg).

Example 6

Under a nitrogen gas flow, to a mixture of NaH (55% in oil, 35 mg) and DMF (4 mL) was added a mixture of N-[(5-chloro-1H-benzimidazol-2-yl)methyl]-2-(5-chloro-2-oxo-1,3-benzothiazol-3(2H)-yl)-N-methylacetamide (335 mg) and DMF (10 mL) under ice-cooling, followed by stirring at room temperature for 30 minutes. The reaction mixture was ice-cooled and methyl iodide (55 µL) was added thereto, followed by stirring at room temperature overnight. The reaction mixture was added to water, followed by extraction with EtOAc. The organic layer was washed with brine and dried over Na₂SO₄, and then concentrated under reduced pressure. To the residue was added chloroform. The resulting solid was collected and then washed with chloroform. To a mixture of the obtained solid and MeOH (3 mL) was added 4 M hydrogen chloride/EtOAc (300 µL), followed by stirring at room temperature. The reaction mixture was concentrated under reduced pressure, and to the residue was added EtOAc. The resulting solid was collected and then washed with EtOAc to obtain N-[(5-chloro-1-methyl-1H-benzimidazol-2-yl)methyl]-2-(5-chloro-2-oxo-1,3-benzothiazol-3(2H)-yl)-N-methylacetamide hydrochloride (60 mg).

Example 7

To a mixture of 2-(5-chloro-2-oxo-1,3-benzoxazol-3(2H)-yl)-N-({5,6-dichloro-1-[2-(methoxymethoxy)ethyl]-1H-benzimidazol-2-yl}methyl)-N-methylacetamide (110 mg) and MeOH (0.22 mL) was added 4 M hydrogen chloride/EtOAc (521 µL), followed by stirring at room temperature overnight. The reaction mixture was concentrated under reduced pressure. The obtained solid was washed with EtOAc to obtain 2-(5-chloro-2-oxo-1,3-benzoxazol-3(2H)-yl)-N-{[5,6-dichloro-1-(2-hydroxyethyl)-1H-benzimidazol-2-yl]methyl}-N-methylacetamide hydrochloride (85 mg).

Example 8

To a mixture of N-{[1-(2-{[tert-butyl(dimethyl)silyl]oxy}ethyl)-1H-benzimidazol-2-yl]methyl}-2-(5-chloro-2-oxo-1,3-benzothiazol-3(2H)-yl)-N-methylacetamide (520 mg) and THF (15 mL) was added tetrabutylammonium fluoride (1.0 M THF solution, 1.43 mL), followed by stirring at room temperature overnight. The reaction mixture was concentrated under reduced pressure. The residue was purified by silica gel column chromatography (eluent: chloroform/MeOH=99/1-90/10). The obtained solid was washed with EtOAc to obtain 2-(5-chloro-2-oxo-1,3-benzothiazol-3(2H)-yl)-N-{[1-(2-hydroxyethyl)-1H-benzimidazol-2-yl]methyl}-N-methylacetamide (340 mg).

In the same manner as the method in Preparation Examples or Examples above, the compounds in Preparation Examples or Examples shown in Tables below were prepared.

TABLE 3

| PEx | Str |
|---|---|
| 1 | 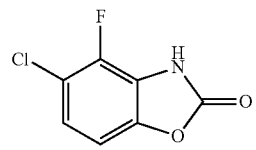 |
| 2 | 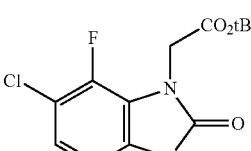 |
| 3 | 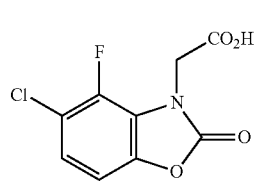 [SMILES: O=C(O)Cn1c(=O)oc2ccc(Cl)c(F)c21] |
| 4 | 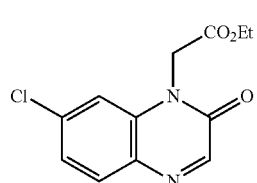 |

TABLE 3-continued

| PEx | Str |
|---|---|
| 5 | 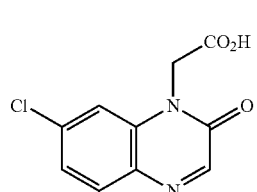 |
| 6 | 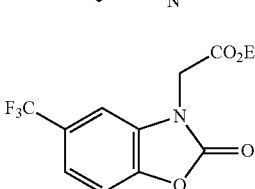 |
| 7 | 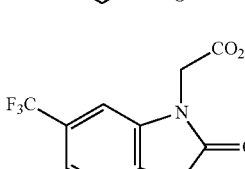 |
| 8 | 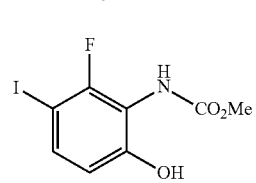 [SMILES: COC(=O)Nc1c(O)ccc(I)c1F] |
| 9 |  |
| 10 | 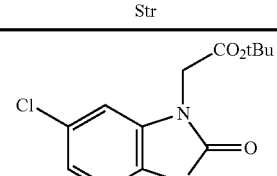 |
| 11 | 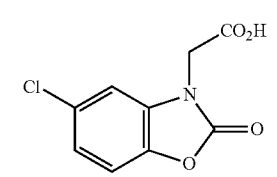 |
| 12 |  |
| 13 | 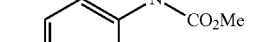 |

TABLE 3-continued

| PEx | Str |
|---|---|
| 14 | 4-fluoro-5-iodo-benzoxazol-2-one with N-CH2CO2tBu |
| 15 | 4-fluoro-5-trifluoromethyl-benzoxazol-2-one with N-CH2CO2tBu |
| 16 | 4-fluoro-5-trifluoromethyl-benzoxazol-2-one with N-CH2CO2H |
| 17 | 5-trifluoromethyl-benzoxazol-2-one (NH) |
| 18 | 5-trifluoromethyl-benzoxazol-2-one with N-CH2CO2Et |

TABLE 4

| PEx | Str |
|---|---|
| 19 | 5-trifluoromethoxy-benzoxazol-2-one with N-CH2CO2H |
| 20 | 5-chloro-benzothiazol-2-one with N-CH2C(O)N(CH3)CH2CO2H |
| 21 | 4,5,6,7-tetrahydro-benzothiazol-2-one with N-CH2C(O)N(CH3)CH2CO2H |
| 22 | 4-trifluoromethyl-benzimidazole with 2-CH2N(CH3)Boc |
| 23 | 5-trifluoromethyl-benzimidazole with 2-CH2N(CH3)Boc |
| 24 | 5-trifluoromethyl-benzimidazole with 2-CH2NH(CH3)·2HCl |
| 25 | 5-chloro-6-fluoro-benzimidazole with 2-CH2N(CH3)Boc |
| 26 | 5-chloro-6-fluoro-benzimidazole with 2-CH2NH(CH3)·2HCl |
| 27 | 5,6-dimethyl-benzimidazole with 2-CH2N(CH3)Boc |
| 28 | 5,6-dimethyl-benzimidazole with 2-CH2NH(CH3)·2HCl |
| 29 | 5,6-difluoro-benzimidazole with 2-CH2N(CH3)Boc |
| 30 | 5,6-difluoro-benzimidazole with 2-CH2NH(CH3)·2HCl |
| 31 | 5-bromo-benzimidazole with 2-CH2N(CH3)Boc |

TABLE 4-continued

| PEx | Str |
|---|---|
| 32 | H3C—NH—CH2—[5-bromo-1H-benzimidazol-2-yl], 2HCl |
| 33 | Boc—N(CH3)—CH2—[5-methyl-1H-benzimidazol-2-yl] |
| 34 | H3C—NH—CH2—[5-methyl-1H-benzimidazol-2-yl], 2HCl |

TABLE 5

| PEx | Str |
|---|---|
| 35 | Boc—N(CH3)—CH2—[5-chloro-6-methyl-1H-benzimidazol-2-yl] |
| 36 | H3C—NH—CH2—[5-chloro-6-methyl-1H-benzimidazol-2-yl], 2HCl |
| 37 | Boc—N(CH3)—CH2—[5-fluoro-1H-benzimidazol-2-yl] |
| 38 | H3C—NH—CH2—[5-fluoro-1H-benzimidazol-2-yl], 2HCl |
| 39 | Boc—N(CH3)—CH2—[4,5-difluoro-1H-benzimidazol-2-yl] |
| 40 | Boc—N(CH3)—CH2—[5,6-dichloro-1H-benzimidazol-2-yl] |

TABLE 5-continued

| PEx | Str |
|---|---|
| 41 | Boc—N(CH3)—CH2—[5-ethoxy-1H-benzimidazol-2-yl] |
| 42 | Boc—N(CH3)—CH2—[4-chloro-1H-benzimidazol-2-yl] |
| 43 | H3C—NH—CH2—[5-trifluoromethoxy-1H-benzimidazol-2-yl], 2HCl |
| 44 | Boc—N(CH3)—CH2—[5-bromo-1-MOM-benzimidazol-2-yl] + Boc—N(CH3)—CH2—[6-bromo-1-MOM-benzimidazol-2-yl] |
| 45 | Boc—N(CH3)—CH2—[5-cyclopropyl-1-MOM-benzimidazol-2-yl] + Boc—N(CH3)—CH2—[6-cyclopropyl-1-MOM-benzimidazol-2-yl] |
| 46 | H3C—NH—CH2—[5-cyclopropyl-1H-benzimidazol-2-yl], 2HCl |
| 47 | Boc—N(CH3)—CH2—[5-methoxy-1H-benzimidazol-2-yl] |

TABLE 6

| PEx | Str |
|---|---|
| 48 | (benzimidazole with OCH3, MOM, N-Boc-N-methylaminomethyl) + (isomer with 6-OCH3) |
| 49 | (benzimidazole with OCH3, Br, MOM, N-Boc-N-methylaminomethyl) + (isomer Br/OCH3) |
| 50 | (5-bromo-6-methoxy-2-(methylaminomethyl)-1H-benzimidazole · 2HCl) |
| 51 | (5,6-dichloro-benzimidazole with N-CH2CO2Et, 2-(N-Boc-N-methylaminomethyl)) |
| 52 | (5,6-dichloro-benzimidazole with N-CH2C(CH3)2OH, 2-(N-Boc-N-methylaminomethyl)) |
| 53 | (5-chloro-benzothiazol-2(3H)-one-N-CH2C(O)N(CH3)CH2-(5-chloro-1H-benzimidazol-2-yl)) |

TABLE 6-continued

| PEx | Str |
|---|---|
| 54 | (5-chloro-benzothiazol-2(3H)-one-N-CH2C(O)N(CH3)CH2-(1H-benzimidazol-2-yl)) |
| 55 | (5-chloro-benzothiazol-2(3H)-one-N-CH2C(O)N(CH3)CH2-(5,6-dichloro-1-(2-MOMO-ethyl)-benzimidazol-2-yl)) |
| 56 | (5-chloro-benzothiazol-2(3H)-one-N-CH2C(O)N(CH3)CH2-(1-(2-OTBDMS-ethyl)-benzimidazol-2-yl)) |
| 57 | (5-chloro-benzoxazol-2(3H)-one-N-CH2C(O)N(CH3)CH2-(1-(2-OTBDMS-ethyl)-benzimidazol-2-yl)) |

TABLE 7

| Ex | Str |
|---|---|
| 1 | (5-chloro-benzoxazol-2(3H)-one-N-CH2C(O)N(CH3)CH2-(5-trifluoromethyl-1H-benzimidazol-2-yl)) · HCl |

TABLE 7-continued

| Ex | Str |
|---|---|
| 2 | (5-chloro-benzothiazol-2-one)-CH2-C(=O)-N(CH3)-CH2-(1H-benzimidazole) |
| 3 | (5-chloro-benzothiazol-2-one)-CH2-C(=O)-N(CH3)-CH2-(5,6-dichloro-1H-benzimidazole) |
| 4 | (5-chloro-benzothiazol-2-one)-CH2-C(=O)-N(CH3)-CH2-(5-chloro-6-fluoro-1H-benzimidazole) · HCl |
| 5 | (5-chloro-benzothiazol-2-one)-CH2-C(=O)-N(CH3)-CH2-(5-chloro-benzoxazole) |
| 6 | (5-chloro-benzothiazol-2-one)-CH2-C(=O)-N(CH3)-CH2-(5-chloro-1-methyl-benzimidazole) · HCl |
| 7 | (5-chloro-benzoxazol-2-one)-CH2-C(=O)-N(CH3)-CH2-(5,6-dichloro-1-(2-hydroxyethyl)-benzimidazole) · HCl |
| 8 | (5-chloro-benzothiazol-2-one)-CH2-C(=O)-N(CH3)-CH2-(1-(2-hydroxyethyl)-benzimidazole) |
| 9 | (5-chloro-benzothiazol-2-one)-CH2-C(=O)-N(CH3)-CH2-(5-chloro-1H-benzimidazole) · HCl |
| 10 | (5-chloro-4,5,6,7-tetrahydro-benzothiazol-2-one)-CH2-C(=O)-N(CH3)-CH2-(5-chloro-1H-benzimidazole) · HCl |
| 11 | (7-chloro-quinoxalin-2-one)-CH2-C(=O)-N(CH3)-CH2-(5-chloro-1H-benzimidazole) |
| 12 | (5-chloro-benzoxazol-2-one)-CH2-C(=O)-N(CH3)-CH2-(5-chloro-1H-benzimidazole) · HCl |

TABLE 8
| Ex | Str |
|---|---|
| 13 | |
| 14 | |
| 15 | |
| 16 | |
| 17 | |
| 18 | |
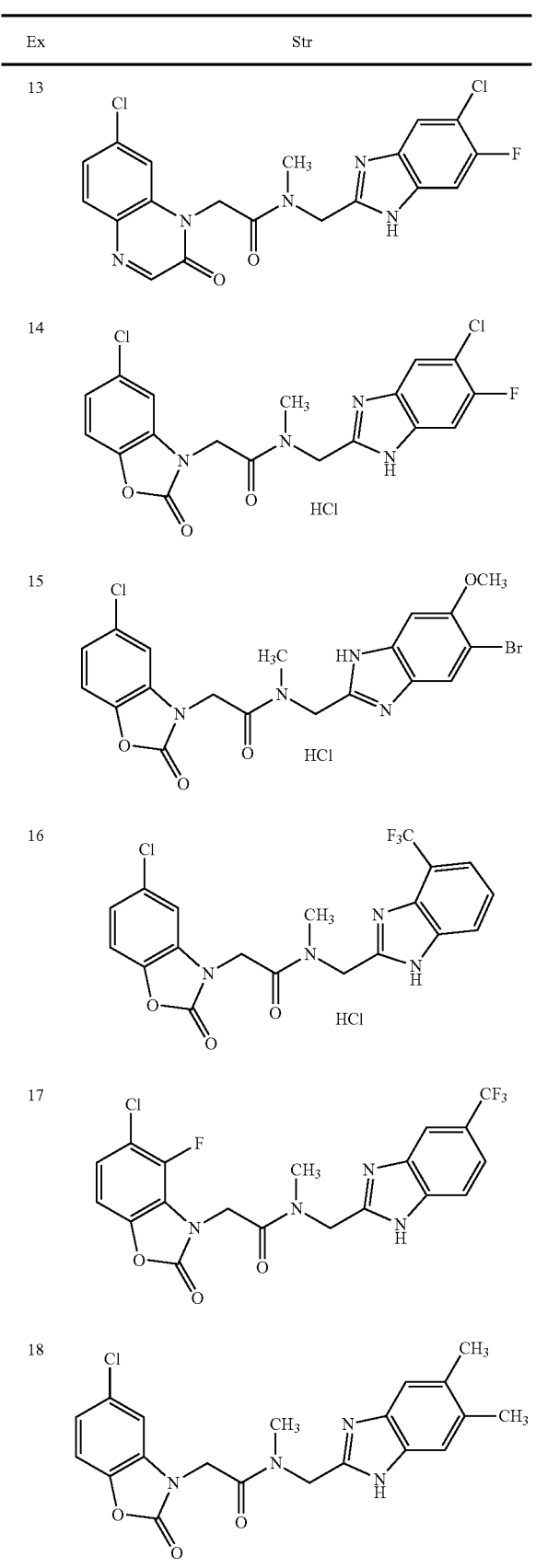
TABLE 8-continued
| Ex | Str |
|---|---|
| 19 | |
| 20 | |
| 21 | |
| 22 | |
| 23 | |
| 24 | |
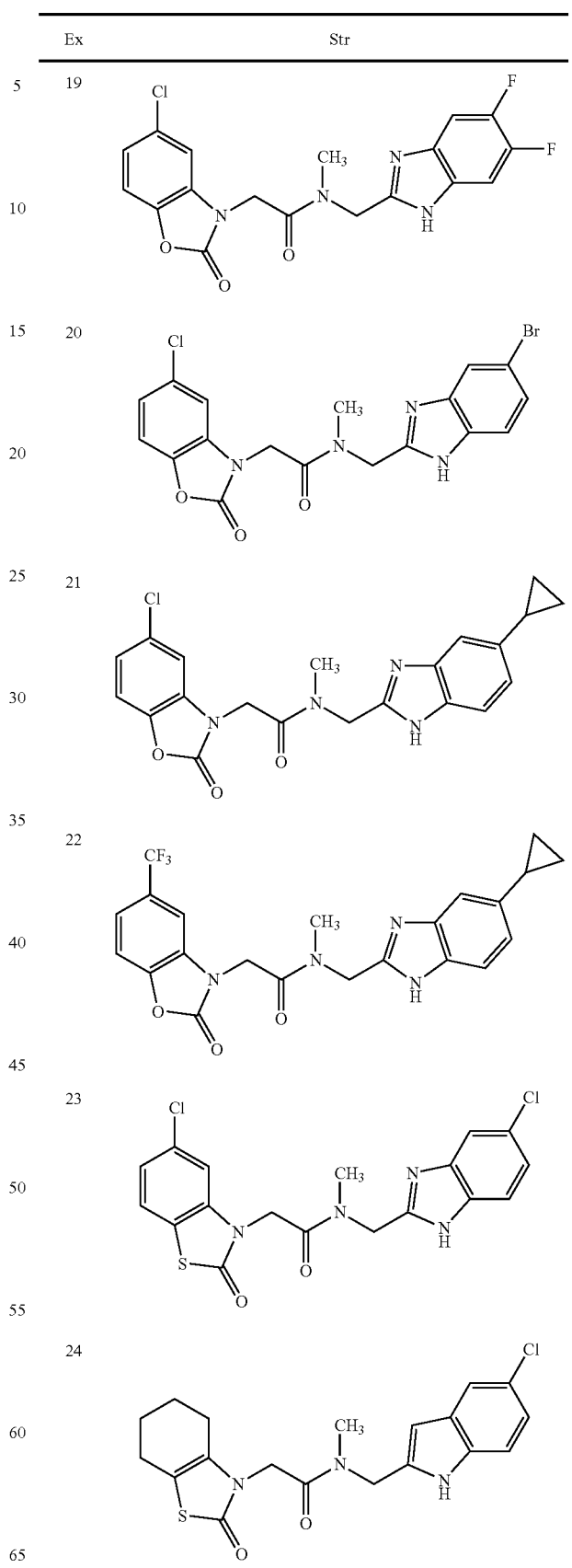

TABLE 9
| Ex | Str |
|---|---|
| 25 | 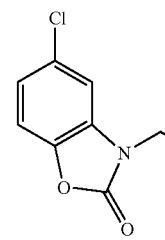 |
| 26 | 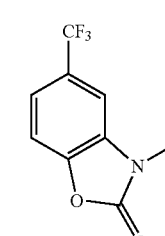 |
| 27 | 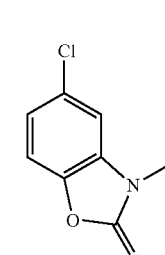 |
| 28 | 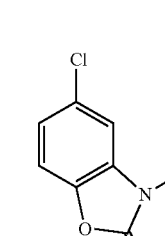 |
| 29 | 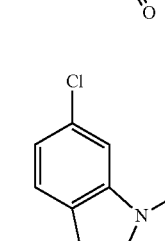 |
| 30 | 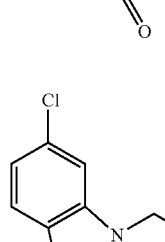 |
TABLE 9-continued
| Ex | Str |
|---|---|
| 31 | |
| 32 | |
| 33 | |
| 34 | |
| 35 | |
| 36 | |

TABLE 10
| Ex | Str |
|---|---|
| 37 | |
| 38 | |
| 39 | |
| 40 | |
| 41 | |
| 42 | |
TABLE 10-continued
| Ex | Str |
|---|---|
| 43 | |
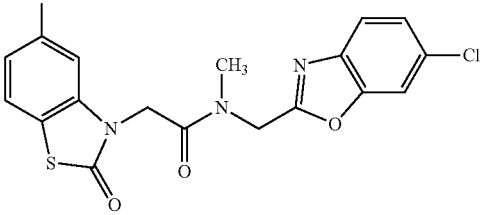
TABLE 11
| PEx | PSyn | DAT |
|---|---|---|
| 1 | 1 | ESI+: 306, 308 (M + Na)+ |
| 2 | 2 | ESI+: 228, 230 |
| 3 | 3 | ESI+: 186 |
| 4 | 4 | ESI+: 220, 222 |
| 5 | 5 | EI+: 187, 189 |
| 6 | 1 | EI+: 301, 303 |
| 7 | 2 | ESI+: 246, 248 |
| 8 | 8 | ESI+: 267, 269 |
| 9 | 9 | ESI+: 239, 241 |
| 10 | 10 | ESI+: 290 |
| 11 | 9 | ESI−: 260 |
| 12 | 12 | ESI+: 312 |
| 13 | 5 | ESI−: 278 |
| 14 | 1 | FAB+: 393 |
| 15 | 15 | EI+: 335 |
| 16 | 2 | ESI−: 278 |
| 17 | 17 | ESI−: 218 |
| 18 | 10 | ESI+: 306 |
| 19 | 9 | ESI+: 278 |
| 20 | 20 | ESI+: 315, 317 |
| 21 | 20 | ESI+: 285 |
| 22 | 22 | ESI+: 330 |
| 23 | 23 | ESI+: 330 |
| 24 | 24 | ESI+: 230 |
| 25 | 23 | ESI+: 314, 316 |
| 26 | 24 | ESI+: 214, 216 |
| 27 | 23 | ESI+: 290 |
| 28 | 24 | ESI+: 190 |
| 29 | 23 | ESI+: 298 |
| 30 | 24 | ESI+: 198 |
| 31 | 23 | ESI+: 340, 342 |
| 32 | 24 | ESI+: 240, 242 |
| 33 | 23 | ESI+: 276 |
| 34 | 24 | ESI+: 176 |
| 35 | 23 | ESI+: 310, 312 |
| 36 | 24 | ESI+: 210, 212 |
| 37 | 23 | ESI+: 280 |
| 38 | 24 | ESI+: 180 |
| 39 | 23 | ESI+: 298 |
| 40 | 23 | ESI+: 330, 332 |
| 41 | 41 | ESI+: 306 |
| 42 | 42 | ESI+: 296, 298 |
| 43 | 43 | APCI/ESI+: 246 |
| 44 | 44 | ESI+: 384, 386 |
| 45 | 45 | ESI+: 346 |
| 46 | 46 | ESI+: 202 |
| 47 | 47 | ESI+: 292 |
| 48 | 44 | ESI+: 336 |
| 49 | 49 | ESI+: 414, 416 |
| 50 | 46 | ESI+: 270, 272 |
| 51 | 51 | ESI+: 416, 418 |
| 52 | 52 | ESI+: 402, 404 |
| 53 | 53 | ESI+: 421, 423 |
| 54 | 53 | ESI+: 371, 373 |
| 55 | 55 | ESI+: 527, 529 |
| 56 | 56 | ESI+: 545, 547 |
| 57 | 56 | ESI+: 529, 531 |

TABLE 12

| Ex | Syn | DAT |
|---|---|---|
| 1 | 1 | ESI+: 439, 441<br>NMR1: 2.95 (3H × ¼, s), 3.32 (3H × ¾, s), 4.93-5.04 (4H, m), 7.16 (1H × ¾, dd, J = 2.2, 8.5 Hz), 7.21 (1H × ¼, dd, J = 2.2, 8.5 Hz), 7.37 (1H × ¾, d, J = 8.5 Hz), 7.41 (1H × ¼, d, J = 8.5 Hz), 7.55 (1H × ¼, d, J = 2.2 Hz), 7.59-7.63 (1H × ¼, m), 7.66 (1H × ¾, d, J = 2.2 Hz), 7.69-7.74 (1H × ¾, m), 7.85 (1H × ¼, d, J = 8.5 Hz), 7.89 (1H × ¾, d, J = 8.5 Hz), 8.05 (1H, br s)<br>$2\theta$ (°) - 5.1, 12.8, 13.6, 14.8, 16.1, 16.5, 18.0, 19.2, 20.7, 23.3 |
| 2 | 2 | ESI+: 387, 389 |
| 3 | 3 | ESI+: 455, 457<br>NMR1: 2.92 (3H × 9/20, s), 3.26 (3H × 11/20, s), 4.73 (2H × 11/20, s), 4.95 (2H × 9/20, s), 5.01 (2H × 11/20, s), 5.09 (2H × 9/20, s), 7.25 (1H × 11/20, dd, J = 2.0, 8.4 Hz), 7.28 (1H × 9/20, dd, J = 2.0, 8.4 Hz), 7.46 (1H × 11/20, d, J = 2.0 Hz), 7.59 (1H × 9/20, d, J = 2.0 Hz), 7.70 (1H × 11/20, d, J = 8.1 Hz), 7.72 (1H × 9/20, d, J = 8.1 Hz), 7.79 (1H, br s), 7.91 (1H, br s)<br>$2\theta$ (°) = 5.5, 9.6, 11.0, 11.5, 13.4, 13.7, 14.2, 16.7, 21.4, 21.9 |
| 4 | 4 | ESI+: 439, 441 |
| 5 | 5 | ESI+: 422, 424 |
| 6 | 6 | ESI+: 435, 437 |
| 7 | 7 | ESI+: 483, 485 |
| 8 | 8 | ESI+: 431, 433 |
| 9 | 1 | ESI+: 421, 423 |
| 10 | 1 | ESI+: 391, 393 |
| 11 | 1 | ESI+: 416, 418 |
| 12 | 1 | ESI+: 405, 407<br>NMR1: 2.95 (3H × ⅕, s), 3.34 (3H × ⅘, s), 4.94-5.05 (4H, m), 7.15 (1H × ⅘, dd, J = 2.2, 8.5 Hz), 7.21 (1H × ⅕, dd, J = 2.2, 8.5 Hz), 7.34-7.88 (5H, m) |
| 13 | 1 | ESI+: 434, 436 |
| 14 | 1 | ESI+: 423, 425 |
| 15 | 1 | ESI+: 479, 481 |
| 16 | PSyn24 + 1 | ESI+: 439, 441<br>NMR1: 2.95 (3H × 2/7, s), 3.31 (3H × 5/7, s), 4.89-5.11 (4H, m), 7.11-8.00 (6H, m) |

TABLE 13

| Ex | Syn | DAT |
|---|---|---|
| 17 | 2 | ESI+: 457, 459<br>NMR1: 2.98 (3H × ⅖, s), 3.23 (3H × ⅗, s), 4.80 (2H × ⅗, s), 4.97 (2H × ⅖, s), 4.98 (2H × ⅗, s), 5.09 (2H × ⅖, s), 7.30-7.38 (2H, m), 7.49 (1H × ⅗, dd, J = 1.5, 8.5 Hz), 7.53 (1H ×+122/5, dd, J = 1.5, 8.5 Hz), 7.71 (1H × ⅗, br d, J = 8.4 Hz), 7.77 (1H × ⅖, br d, J = 8.4 Hz), 7.88 (1H × ⅗, br s), 7.94 (1H × ⅖, br s) |
| 18 | 2 | ESI+: 399, 401 |
| 19 | 2 | ESI+: 407, 409 |
| 20 | 2 | ESI+: 449, 451<br>NMR1: 2.92 (3H × ⅖, s), 3.21 (3H × ⅗, s), 4.74 (2H × ⅗, s), 4.91 (2H × ⅖, s), 4.92 (2H × ⅗, s), 4.98 (2H × ⅖, s), 7.18 (1H × ⅗, dd, J = 2.2, 8.5 Hz), 7.21 (1H ×+122/5, dd, J = 2.2, 8.5 Hz), 7.28-7.42 (2H, m), 7.45-7.89 (3H, m)<br>$2\theta$ (°) = 8.1, 9.8, 10.9, 11.4, 13.4, 15.2, 16.0, 16.3, 20.6, 26.9 |
| 21 | 2 | ESI+: 411, 413 |
| 22 | 2 | ESI+: 445 |
| 23 | 2 | ESI+: 420, 422 |
| 24 | 2 | ESI+: 390, 392 |
| 25 | 2 | ESI+: 439, 441<br>NMR1: 2.93 (3H × ⅖, s), 3.23 (3H × ⅗, s), 4.74 (2H ×+123/5, s), 4.91 (2H × ⅖, s), 5.01 (2H ×+123/5, s), 5.08 (2H × ⅖, s), 7.18 (1H × ⅗, dd, J = 2.0, 8.5 Hz), 7.25 (1H × ⅖, dd, J = 2.0, 8.5 Hz), 7.45-7.78 (5H, m) |
| 26 | 2 | ESI+: 455, 457 |
| 27 | 2 | ESI+: 491 |
| 28 | 2 | ESI+: 389, 391 |
| 29 | 2 | ESI+: 385, 387 |
| 30 | 2 | ESI+: 419, 421 |
| 31 | 2 | ESI+: 455, 457 |
| 32 | 2 | ESI+: 423 |
| 33 | PSyn24 + 2 | ESI+: 415, 417 |
| 34 | PSyn24 + 2 | ESI+: 405, 407 |
| 35 | PSyn24 + 2 | ESI+: 407, 409 |
| 36 | PSyn24 + 2 | ESI+: 439, 441 |

TABLE 14

| Ex | Syn | DAT |
|---|---|---|
| 37 | PSyn24 + 2 | ESI+: 511, 513<br>NMR1: 1.09 (6H × 11/20, s), 1.19 (6H × 9/20, s), 2.93 (3H × 9/20, s), 3.22 (3H × 11/20, s), 4.17 (2H × 11/20, s), 4.22 (2H × 9/20, s), 4.78-5.11 (5H, m), 7.16-7.23 (1H, m), 7.37-7.50 (2H, m), 7.86-8.11 (2H, m) |
| 38 | PSyn24 + 2 | ESI+: 439, 441 |
| 39 | PSyn24 + 2 | ESI+: 473 |
| 40 | 8 | ESI+: 415, 417 |
| 41 | 3 | ESI+: 425, 427 |
| 42 | 4 | ESI+: 409, 411 |
| 43 | 5 | ESI+: 422, 424 |

INDUSTRIAL APPLICABILITY

A compound of the formula (I) or a salt thereof has a dopamine D1 receptor positive allosteric modulating activity, and can be used as an agent for preventing and/or treating cognitive impairment, negative symptoms of schizophrenia, Parkinson's disease, Alzheimer's disease, Huntington's disease, drug addictions, or the like.

The invention claimed is:
1. A compound of the formula (I) or a salt thereof:

[Chem. 13]

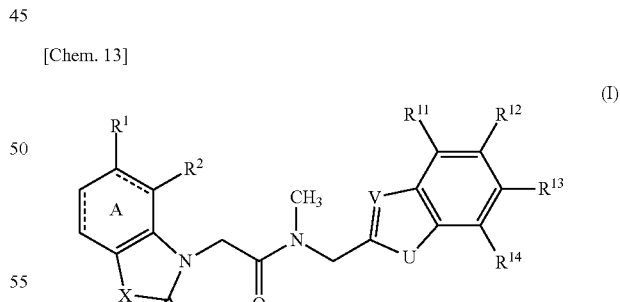

wherein
ring A is a benzene ring,
$R^1$ is lower alkyl, halogen, halogeno-lower alkyl, or —O-halogeno-lower alkyl,
$R^2$ is H or halogen,
$R^{11}$, $R^{12}$, $R^{13}$ and $R^{14}$ are the same as or different from each other, and are H, lower alkyl, halogen, halogeno-lower alkyl, cycloalkyl, —O-lower alkyl, or —O-halogeno-lower alkyl, U is NR$^{15}$ or O,
V is CH or N,
in the case where U is O, V is N,
R$^{15}$ is H, lower alkyl, or -lower alkylene-OH, and
X is O.

2. The compound or a salt thereof according to claim 1, wherein
U is NR$^{15}$, and
V is N.

3. The compound or a salt thereof according to claim 2, wherein
R$^1$ is halogen, halogeno-lower alkyl, or —O-halogeno-lower alkyl, and
R$^{11}$, R$^{12}$, R$^{13}$, and R$^{14}$ are the same as or different from each other, and are H, halogen, halogeno-lower alkyl, cycloalkyl, or —O-halogeno-lower alkyl.

4. The compound or a salt thereof according to claim 3, wherein R$^{15}$ is H.

5. The compound or a salt thereof according to claim 4, wherein R$^1$ is halogen or halogeno-lower alkyl.

6. The compound or a salt thereof according to claim 5, wherein R$^{11}$, R$^{12}$, R$^{13}$ and R$^{14}$ are the same as or different from each other, and are H, halogen, or halogeno-lower alkyl.

7. The compound or a salt thereof according to claim 6, wherein R$^{12}$ is halogen or halogeno-lower alkyl, and R$^{11}$, R$^{13}$ and R$^{14}$ are H.

8. The compound or a salt thereof according to claim 7, which is selected from the following group consisting of:
2-(5-chloro-2-oxo-1,3-benzoxazol-3(2H)-yl)-N-methyl-N-{[5-(trifluoromethyl)-1H-benzimidazol-2-yl]methyl}acetamide,
N-[(5-chloro-1H-benzimidazol-2-yl)methyl]-2-(5-chloro-2-oxo-1,3-benzoxazol-3(2H)-yl)-N-methylacetamide,
2-(5-chloro-4-fluoro-2-oxo-1,3-benzoxazol-3(2H)-yl)-N-methyl-N-{[5-(trifluoromethyl)-1H-benzimidazol-2-yl]methyl}acetamide,
N-[(5-bromo-1H-benzimidazol-2-yl)methyl]-2-(5-chloro-2-oxo-1,3-benzoxazol-3(2H)-yl)-N-methylacetamide, and
N-[(5-chloro-1H-benzimidazol-2-yl)methyl]-N-methyl-2-[2-oxo-5-(trifluoromethyl)-1,3-benzoxazol-3(2H)-yl]acetamide,
or a salt thereof.

9. The compound or a salt thereof according to claim 8, which is 2-(5-chloro-2-oxo-1,3-benzoxazol-3(2H)-yl)-N-methyl-N-{[5-(trifluoromethyl)-1H-benzimidazol-2-yl]methyl}acetamide hydrochloride.

10. The compound or a salt thereof according to claim 8, which is 2-(5-chloro-4-fluoro-2-oxo-1,3-benzoxazol-3(2H)-yl)-N-methyl-N-{[5-(trifluoromethyl)-1H-benzimidazol-2-yl]methyl}acetamide.

11. The compound or a salt thereof according to claim 8, which is N-[(5-bromo-1H-benzimidazol-2-yl)methyl]-2-(5-chloro-2-oxo-1,3-benzoxazol-3 (2H)-yl)-N-methylacetamide.

12. A pharmaceutical composition comprising the compound or a salt thereof according to claim 1, and a pharmaceutically acceptable excipient.

* * * * *